United States Patent [19]

Matsuno et al.

[11] Patent Number: 5,766,184
[45] Date of Patent: Jun. 16, 1998

[54] ENDOSCOPIC TREATMENT TOOL

[75] Inventors: Kiyotaka Matsuno, Hachiouji; Yukio Sato, Kodaira; Akihito Sadamasa; Minoru Shinozuka, both of Hachiouji, all of Japan; Yutaka Yanuma, New York, N.Y.

[73] Assignee: Olympus Optical Co., Ltd., Tokyo, Japan

[21] Appl. No.: 669,479

[22] PCT Filed: Nov. 2, 1995

[86] PCT No.: PCT/JP95/02244

§ 371 Date: Jul. 1, 1996

§ 102(e) Date: Jul. 1, 1996

[87] PCT Pub. No.: WO96/14020

PCT Pub. Date: May 17, 1996

[30] Foreign Application Priority Data

Nov. 2, 1994 [JP] Japan ................... 6-269362
Apr. 13, 1995 [JP] Japan ................... 7-088281

[51] Int. Cl.[6] .................................. A61B 17/10
[52] U.S. Cl. ............... 606/142; 606/1; 606/108; 606/167; 606/171; 606/177; 606/185; 606/213; 606/148; 606/144; 606/151; 606/139; 604/95; 604/15; 604/158
[58] Field of Search ................ 604/95, 159, 158, 604/164, 11, 15–18; 606/1, 108, 110, 113, 167, 170, 171, 176, 177, 180, 185, 213, 148, 147, 145, 144, 139, 151

[56] References Cited

U.S. PATENT DOCUMENTS

| | | | |
|---|---|---|---|
| 3,958,576 | 5/1976 | Komiya | 606/142 |
| 4,018,229 | 4/1977 | Komiya | 606/139 |
| 4,043,323 | 8/1977 | Komiya . | |
| 4,633,871 | 1/1987 | Shinozuka . | |
| 5,049,154 | 9/1991 | Quadri . | |
| 5,066,295 | 11/1991 | Kozak et al. . | |
| 5,185,004 | 2/1993 | Lashinski | 604/95 |
| 5,263,958 | 11/1993 | deGuillebon et al. | 606/167 |
| 5,342,394 | 8/1994 | Matsuno et al. . | |
| 5,454,821 | 10/1995 | Harm et al. | 606/139 |
| 5,578,045 | 11/1996 | Das | 606/213 |

FOREIGN PATENT DOCUMENTS

| | | |
|---|---|---|
| 0027704 A2 | 4/1981 | European Pat. Off. . |
| 4136861 C2 | 5/1993 | Germany . |
| 63-145641 | 6/1988 | Japan . |
| 64-2639 | 1/1989 | Japan . |
| 3-195547 | 8/1991 | Japan . |
| 5-62214 | 8/1993 | Japan . |
| 6-178781 | 6/1994 | Japan . |
| 8-150145 | 6/1996 | Japan . |
| WO 90/05491 | 5/1990 | WIPO . |
| WO 92/11815 | 7/1992 | WIPO . |

*Primary Examiner*—Michael Buiz
*Assistant Examiner*—Tina T. D. Pham
*Attorney, Agent, or Firm*—Frishauf, Holtz, Goodman, Langer & Chick

[57] ABSTRACT

An endoscopic treatment tool according to the present invention is led into the body through the endoscope channel. A treatment section (2) is operated by transmitting the operating power of an operating section (4) on the operator's side to the treatment section (2) at the forward end thereof. The endoscopic treatment tool is characterized in that a tubular sheath (28) is adapted to be inserted into the endoscope channel, rotative operation means (55) is arranged in the operating section (4) for rotatively operating the treatment section (2), and an operating wire (33) is rotatably inserted into the sheath (28) and has a torque transmissivity for coupling the treatment section (2) and the rotative operation means (55) and capable of transmitting the rotation torque from the rotative operation means (55) to the treatment section (2).

23 Claims, 12 Drawing Sheets

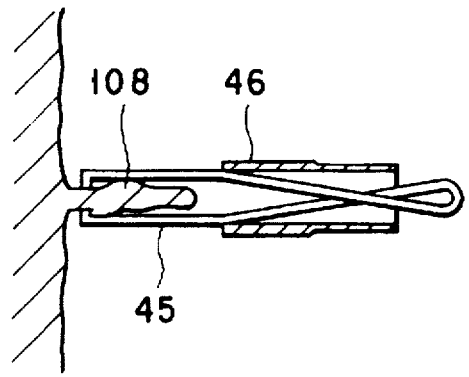
F I G. 15A
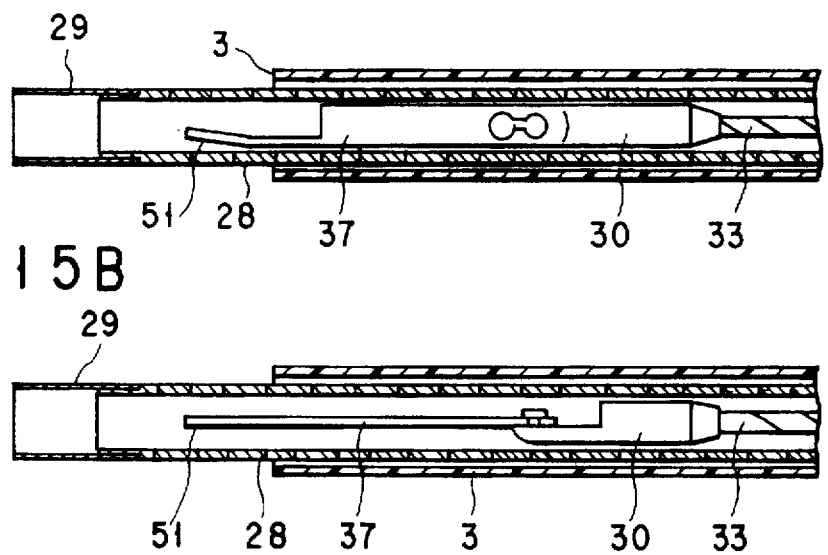
F I G. 15B
F I G. 15C
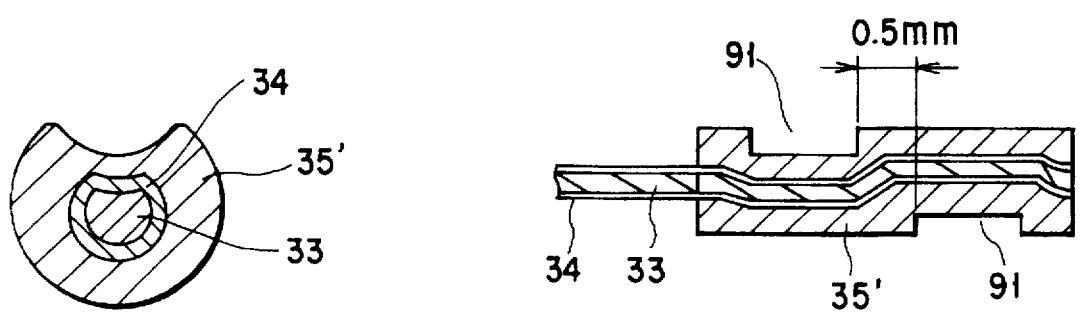
F I G. 17
F I G. 18
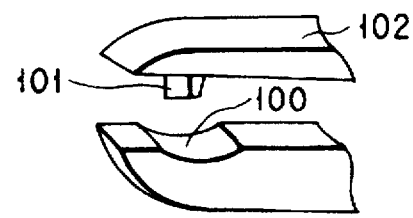
F I G. 19

ENDOSCOPIC TREATMENT TOOL

BACKGROUND OF THE INVENTION

The present invention relates to an endoscopic treatment tool inserted into the body cavity through an endoscope for performing a treatment or the like.

A conventional endoscopic treatment tool such as described above comprises at the forward end thereof a treatment section for treating or performing biopsy on a vital tissue or holding the tissue, which treatment section is so structured as to open or otherwise operate similarly taking advantage of the spring characteristics or a link mechanism.

Such a tool has the disadvantage that the treatment section cannot be operated in optimum direction with respect to a foreign matter or the tissue on which biopsy or the holding operation is to be performed, with the result that the tissue and foreign matters cannot be successfully treated.

In view of this, JP-A-55-109501 discloses a treatment tool comprising a sheath section formed of multi-turn coil or a multiple coils inserted in the channel of the endoscope for connection with the treatment section, which sheath section is rotated on the operator's side so that the treatment section can be rotated in the desired direction and thus can be operated in the optimum direction.

In the case where the sheath section is inserted into the channel of the endoscope and rotated, however, the friction resistance between the outer periphery of the sheath section and the inner wall of the channel causes a skip or like irregularities in rotation, thereby sometimes making it impossible to transmit the turning effort positively to the treatment section at the forward end.

Also, forming a sheath section of a multi-turn coil or multiple coils reduces the flexibility of the sheath section. In the case where a high efficiency in rotation characteristics is sought, the insertion characteristic of the sheath section with respect to the channel is extremely deteriorated, thereby making it difficult to achieve the desired rotation characteristics. Especially, a multi-turn coil has the disadvantage that it cannot be rotated depending on the direction in which the coil is wound.

The sheath section of multiple coils, on the other hand, which is formed of several layers of coils overlapped on each other, leads to the disadvantage of an often increased diameter compared with a single coil. A sheath section formed of a multi-turn coil is a problem when considering the fact that the sheath section and the treatment section at the forward end thereof are led into the body cavity using the limited space defined by the channel of the endoscope.

SUMMARY OF THE INVENTION

The present invention has been developed in view of the above-mentioned situations, and the object thereof is to provide an endoscopic treatment tool which is capable of transmitting the turning effort to the treatment section at the forward end positively without thickening the sheath portion or adversely affecting the other functions.

In order to solve the above-mentioned problem, according to the invention, there is provided an endoscopic treatment tool which is led into the body through the endoscope channel to operate the treatment section by transmitting the operating force of the operating section from the operator's side to the treatment section at the forward end, comprising a tubular sheath adapted to be inserted into the endoscope channel, rotative operation means mounted on the operating section for rotatively operating the treatment section, and an operating wire inserted rotatably into the sheath for coupling the treatment section to the rotative operation means and having such a torque transmissivity capable of transmitting the rotation torque from the rotative operation means to the treatment section.

In this configuration, rotation of the operating wire by operating the rotative operation means rotates the forward-end treatment section with the rotation of the operating wire, thereby making it possible to orient the treatment section in a given direction. In this case, since the operating wire is inserted into the tubular sheath, the rotation of the operating wire and the resulting friction resistance between the inner wall of the endoscope channel and the operating wire causes no skip or other irregularities in rotation, and therefore the turning effort due to the rotative operation means can be positively transmitted to the forward-end treatment section.

BRIEF DESCRIPTION OF DRAWINGS

FIG. 15A is a sectional view of a clip retained in the tissue to be bound, FIG. 15B a cross sectional view of a clip device after a clip is retained, and FIG. 15C a longitudinal sectional view of a clip device after a clip is retained.

FIG. 17 is a front sectional view showing the state of a caulked portion of the base end of the operating wire.

FIG. 18 is a side sectional view showing a caulked portion of the base end of the operating wire.

FIG. 19 is a diagram showing the essential parts of a caulking tool.

DETAILED DESCRIPTION

Embodiments of the invention will be described below with reference to the drawings.

Figure 1A:
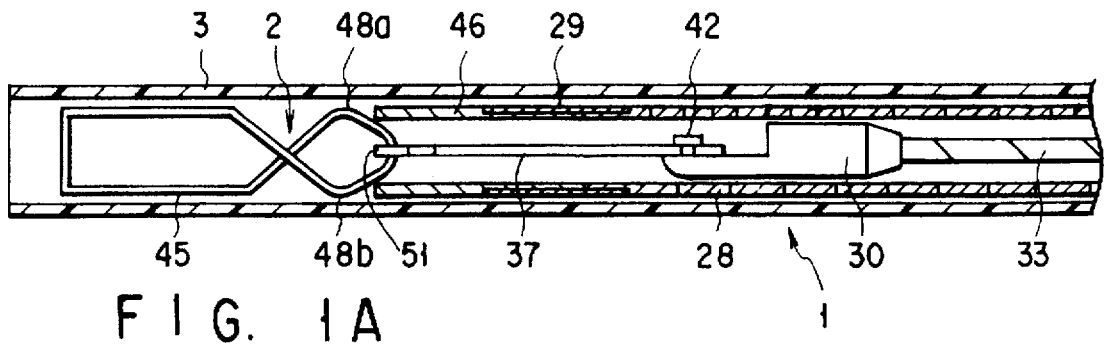
FIG. 1A is a longitudinal sectional view of the forward end of a clip device according to a first embodiment of the invention.
Figure 1B:
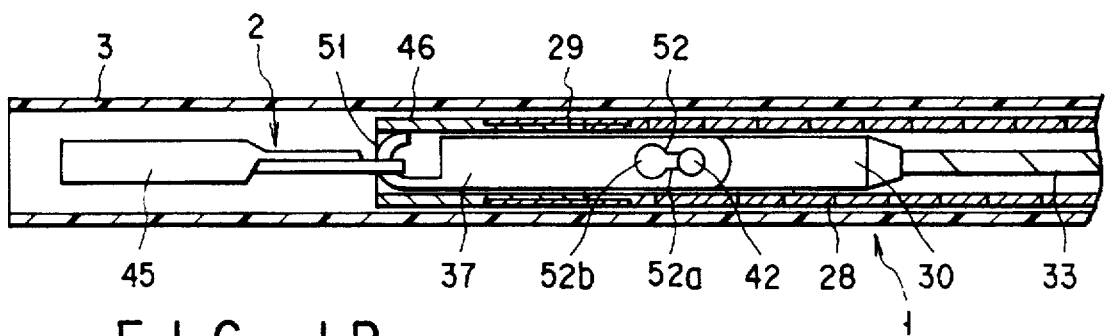
FIG. 1B is a cross sectional view showing the forward end of the clip device.

FIGS. 1 to 15 show a first embodiment of the invention. FIGS. 1A and 1B show the forward end of a clip device as an endoscopic treatment tool, and FIG. 2 an operating unit 4 on the operator's side of the tool. As shown in FIGS. 1A and 1B, this clip device includes a clip device proper 1 and a cassette-type clip unit 2 mounted replaceably on the clip device proper 1. In these drawings, numeral 3 designates a lead tube for the clip device proper 1. This lead tube 3 is formed of a flexible material such as ethylene tetrafluoride resin or the like and is adapted to be inserted into a body cavity using, for example, the channel of the endoscope.

Figure 2:
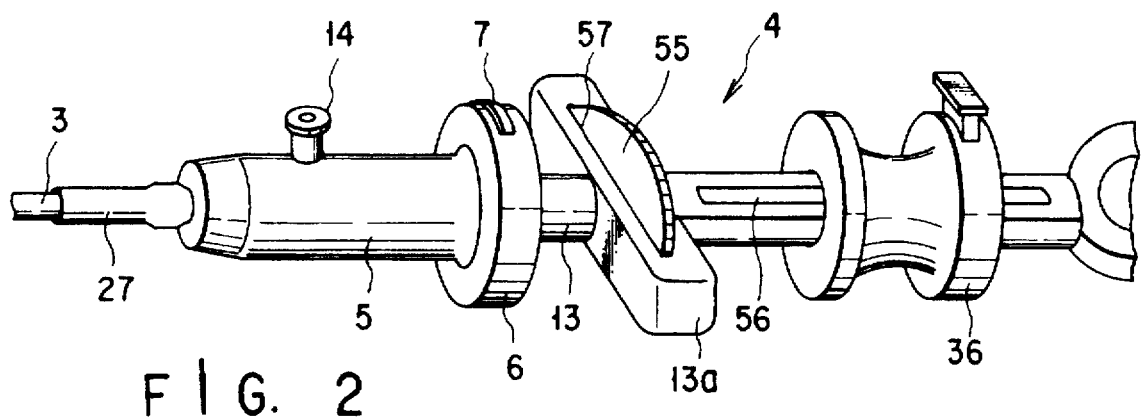
FIG. 2 is a perspective view of the operating section of a clip device.

As shown in FIG. 2, the operating unit 4 of the clip device proper 1 includes an operating unit proper 5, a first slider 13 mounted axially slidably in the operating unit proper 5, and a second slider 36 axially slidable with respect to the first slider 13 through a ratchet mechanism. The base end of the lead tube 3 is coupled to the operating unit proper 5 as described later.

As shown in FIGS. 1A and 1B, a flexible operating tube 28 having a coupling ring 29 of a stainless-steel short tube fixedly mounted at the forward end thereof is retractively inserted in the lead tube 3. As described later, this operating tube 28 is formed of densely-wound stainless-steel wires, for example, the base end of which is coupled to the first slider 13 of the operating unit 4. With the operation of the first slider 13, the operating tube 28 is caused to extend or retract in the lead tube 3 and also is adapted to protrude or withdraw through the forward-end opening of the lead tube 3.

An operating wire 33 having a torque transmissivity is retractively inserted in the operating tube 28. This operating wire 33 is coated with fluororesin or the like material having a superior slidability over the entire length thereof, and the superior operability of the operating wire 33 is thereby maintained.

Figure 3A:
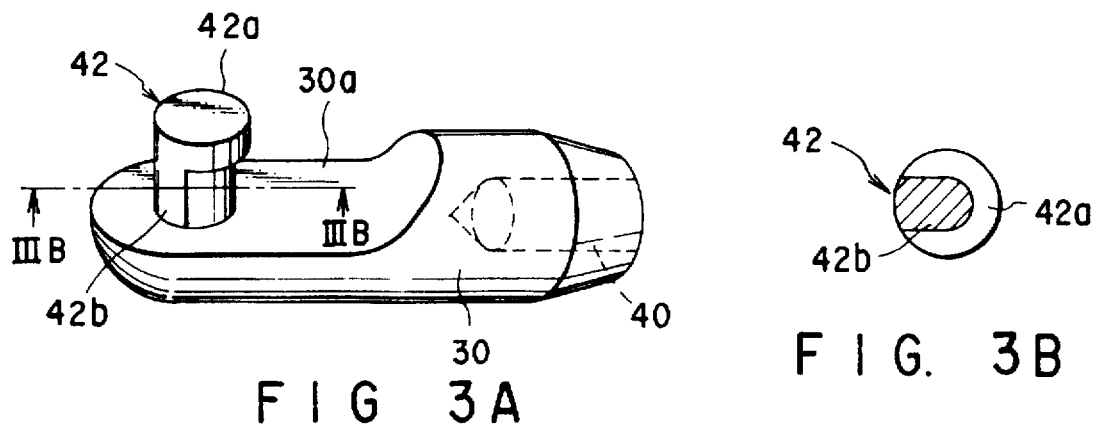
FIG. 3A is a perspective view of a hook section.
Figure 3B:
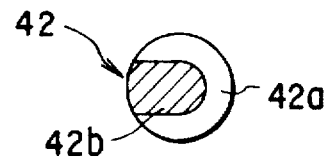
FIG. 3B is a sectional view taken in line IIIB—IIIB in FIG. 3A.

As shown in FIG. 1, the forward end of the operating wire 33 has mounted thereon a hook 30 adapted to replaceably engage a coupling plate 37 of the cassette-type clip unit 2. FIG. 3A is a perspective view showing the hook 30 in enlarged form. As shown, the hook 30 has formed thereon a recess 30a on one side of the forward-end solid-cylindrical portion thereof. A pin 42 is erected from the recess 30a perpendicularly to the length of the hook 30. This pin 42 includes a circular head 42a and a neck 42b smaller in diameter than the head 42a. By the way, FIG. 3B is a sectional view taken in line IIIB—IIIB in FIG. 3A.

A hole 40 coaxial with the longitudinal center axis of the hook 30 is formed in the base end of the hook 30. An operating wire 33 is inserted into and fixed by a fixing material or the like in the hole 40.

The hook 30 is formed by metal injection molding. This is because a metal injection mold is superior in tenacity (toughness) to a machine-ground product, and should a force more than necessary be imposed on it, the mold is only deformed but not broken off from the wire 33.

The lead tube 3 is desirably transparent so that the operating tube 28 inserted in the lead tube 3 is visible by endoscope from outside the lead tube 3. The clearance between the lead tube 3 and the operating tube 28 is preferably about 0.1 to 0.5 mm over the whole periphery. The reason is that an excessively large clearance would deform or buckle the tubes 3 and 28 while an excessively small clearance would increase the sliding resistance between the tubes 3 and 28.

Figure 4:
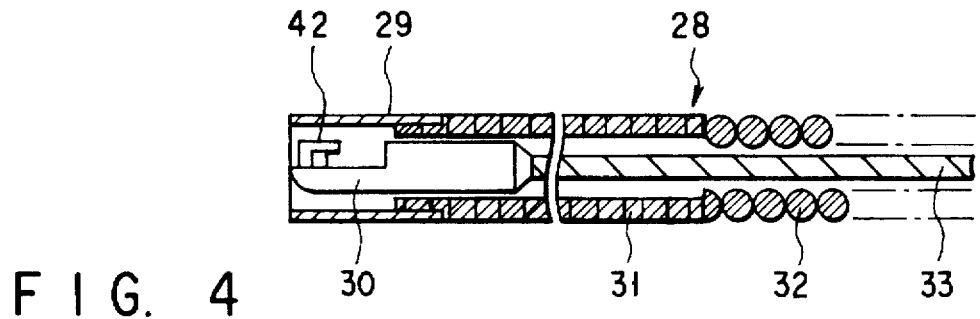
FIG. 4 is a side sectional view showing a configuration of an operating tube.

As shown in FIG. 4, the operating tube 28 includes a forward-end coil 31 formed of a densely-wound stainless-steel wire of a rectangular section and having such an inner diameter that the hook 30 can be inserted in it, and a base-end coil 32 connected to the forward-end coil 31 by laser welding or the like process and having a densely-wound stainless-steel wire of a circular section. In this way, the forward-end coil 31 is formed flat in view of the need of securing such an inner diameter that the hook can be inserted in it. The flat-coil structure, though thin in thickness, assures a durability against expansion and contraction and a high tenacity.

The clearance between the base-end coil 32 of the operating tube 28 and the operating wire 33 inserted therein is set at a minimum. This clearance is desirably about 0.05 to 0.2 mm. This is in order to prevent the operating wire 33 from zigzagging within the base-end coil 32 and thereby adversely affecting the force-transmitting capability.

Figure 5A:
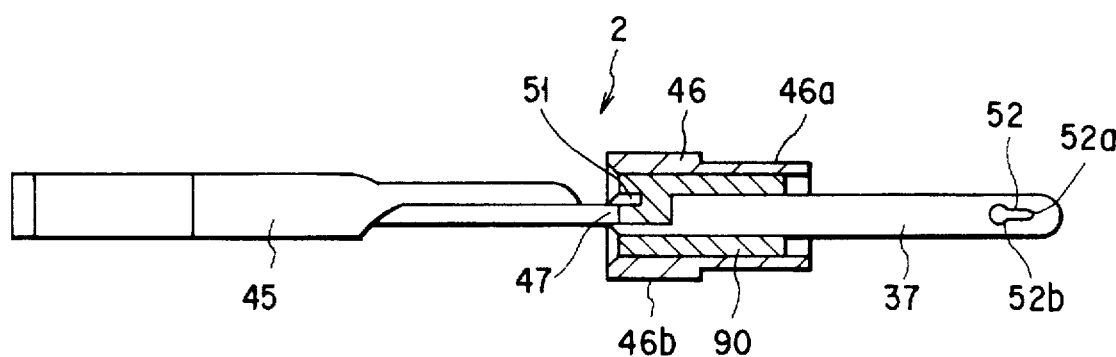
FIG. 5A is a plan view of a clip, and FIG. 5B a side view of the clip.
Figure 5B:
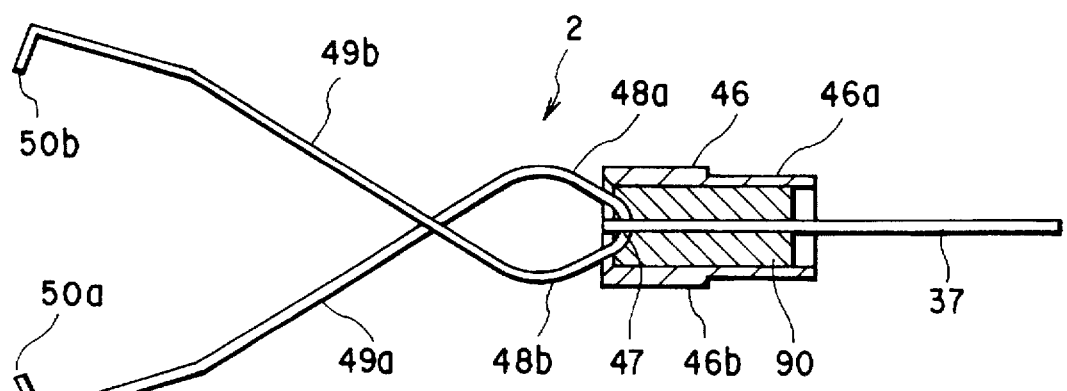

As shown in FIGS. 5A and 5B, the clip unit 2 includes a clip or clamp 45, a coupling plate 37 constituting a coupling member removably coupled to the clip 45, and a clip-fastening ring 46.

The clip 45 is constructed of a thin band plate of stainless steel bent at the center thereof with the bent portion thereof making up a base end 47. A pair of loosely-fitted portions 48a, 48b spaced wider than the inner diameter of the clip-fastening ring 46 are extended from the base end 47. Further, the loosely-fitted portions 48a, 48b are so extended that arms 49a, 49b intersect each other. Furthermore, the forward end of the arms 49a, 49b forms holding sections 50a, 50b bent toward each other. The arms 49a, 49b of the clip 45 have a tendency to open the holding sections 50a, 50b.

On the other hand, the coupling plate 37 is formed by punching a thin band plate of stainless steel, and has an end thereof formed with a J-shaped hook removably engaging the base end 47 of the clip 45 as shown in FIG. 5A. Also, an engaging hole 52 is formed to removably engage the pin 42 (FIGS. 1A, 1B and 3A) of the hook 30 in the vicinity of the other end of the coupling plate 37. This engaging hole 52 includes a long hole portion 52a extending lengthwise and a large-diameter hole portion 52b formed at the end of the hole portion 52a nearer to the hook 51. The head 42a of the pin 42 of the hook 30 is formed smaller than the large hole portion 52b of the engaging hole 52 and larger than the width of the hole portion 52a. The neck 42b of the pin 42 is formed smaller in diameter than the width of the long hole portion 52a of the engaging hole 52.

The clip-fastening ring 46, on the other hand, as shown in FIGS. 1A and 1B, is removably mounted on the coupling ring 29 at the forward end of the operating tube 28. As described later, the clip-fastening clip 46 is fitted to cover the arms 49a, 49b of the clip 45 thereby to close the holding sections 50a, 50b of the clip 45.

As shown in FIGS. 5A and 5B, an unevenness is formed by a step on the outer peripheral surface of the clip-fastening ring 46. The small-diameter section 46a of the clip-fastening ring 46 formed by this step has an outer diameter smaller than the inner diameter of the coupling ring 29 of the operating tube 28 (FIG. 1) and is coupled by being fitted in the coupling ring 29. Incidentally, the outer diameter of the large-diameter section 46b of the clip-fastening ring 46 is thicker than the inner diameter of the coupling ring 29.

Also, as shown in FIGS. 5A and 5B, the cassette-type clip unit 2 has the coupling plate 37 thereof inserted into the clip-fastening ring 46 from the large-diameter section 46b with the hook 51 of the coupling plate 37 engaged in the base end 47 of the clip 45. Under this condition, a fixing agent 90 such as silicon is filled in the clip-fastening ring 46, whereby the clip 45 and the coupling plate 37 are tacked in the clip-fastening ring 46.

Now, the operating unit 4 of the tool proper 1 will be described in detail with reference to FIGS. 6 to 13.

Figure 6:
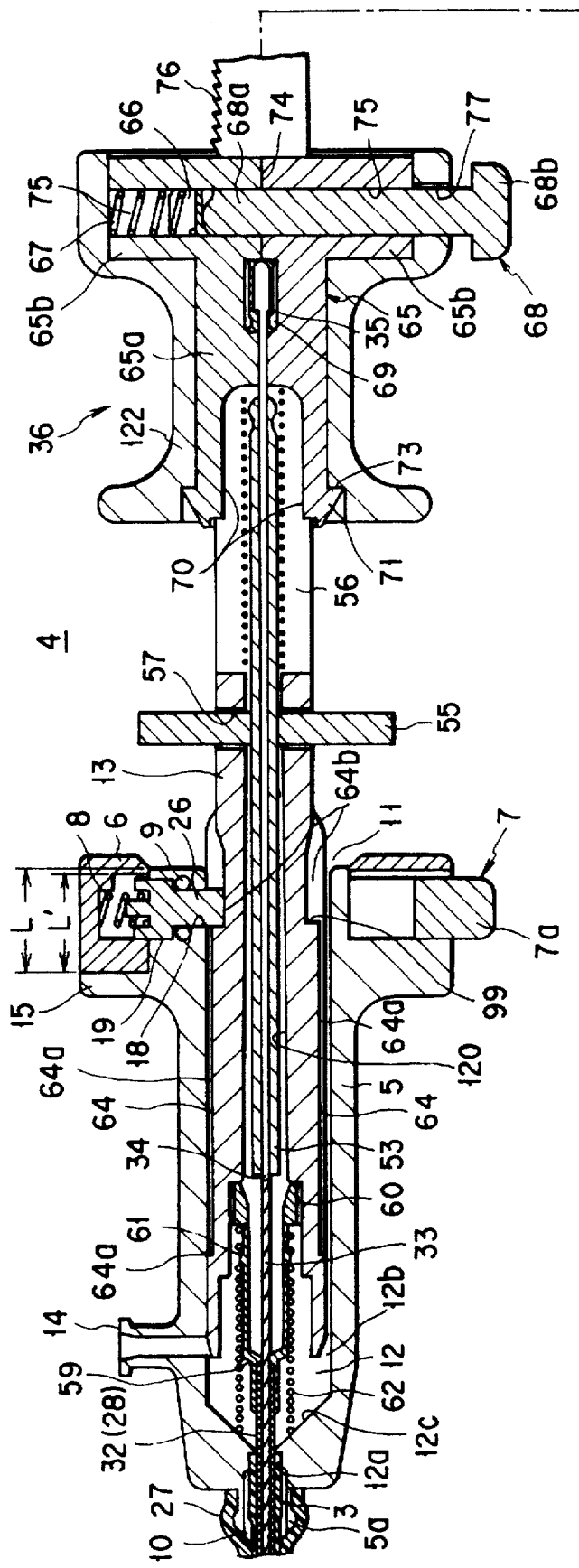
FIG. 6 is a sectional view of an operating unit of the clip device.
Figure 6:
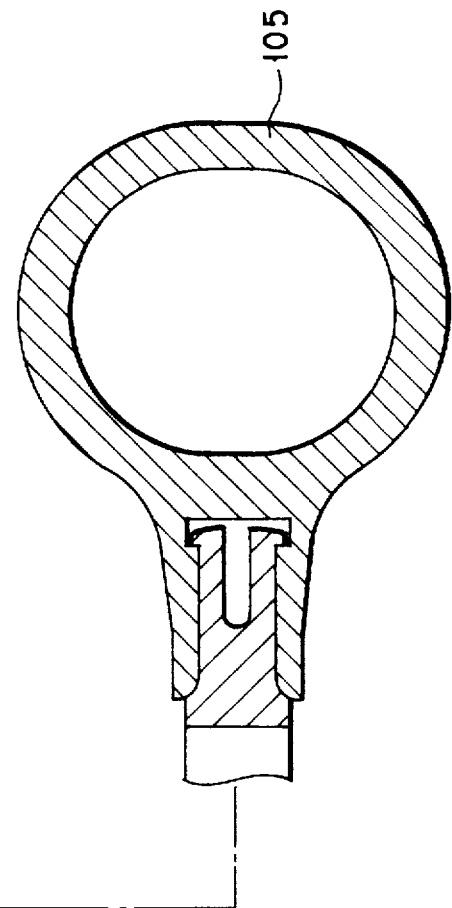

As shown in FIG. 6, the operating unit 4 includes an operating unit proper 5, a first slider 13 slidably mounted in axial direction in the operating unit proper 5, and a second slider 36 slidable in axial direction through a ratchet mechanism with respect to the first slider 13.

The operating unit 5 has formed over the entire length thereof a through hole 12 terminating with a forward-end opening 10 and a base-end opening 11. This through hole 12 communicates with the inner hole of the lead tube 3 connected to the forward-end opening 10 of the operating unit proper 5. Also, a heat-contraction tube 27 of a comparatively soft material such as silicon is covered over the outer periphery of the forward-end socket 5a of the operating unit proper 5 from the outer periphery of the base end of the lead tube 3 (see also FIG. 2). This is in order to prevent the lead tube 3 from buckling due to an extreme alteration of the hardness at the connection between the lead tube 3 and the operating unit proper 5. The heat-contraction tube 27 functions as a reinforcing member for smoothing the hardness change from the lead tube 3 to the operating unit proper 5.

The through hole 12 has a small-diameter portion 12a at the forward end thereof and a large-diameter portion 12b occupying a majority of the remaining portions. The small-diameter portion 12a and the large-diameter portion 12b are connected to each other through a tapered hole 12c. The large-diameter portion 12b is formed with such an inner diameter that the forward end of the first slider 13 can be inserted into it. Also, the operating unit proper 5 has formed thereon a lure lock socket 14 onto which an injection cylinder not shown can be removably fitted and which communicates with the large-diameter portion 12b of the through hole 12.

Figure 7:
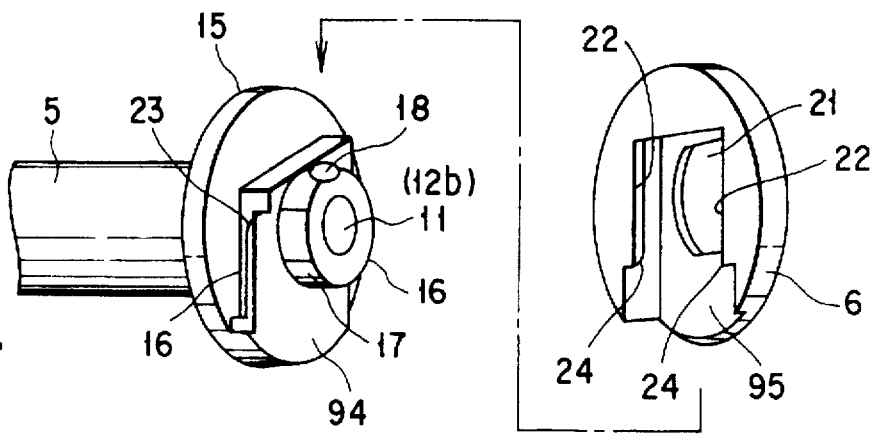
FIG. 7 is a perspective view showing a configuration of the operating unit proper and a lid member.
Figure 8:
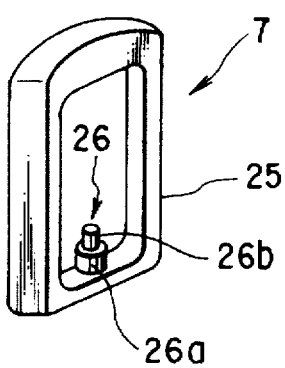
FIG. 8 is a perspective view showing a button for releasing a fixed state.
Figure 10:
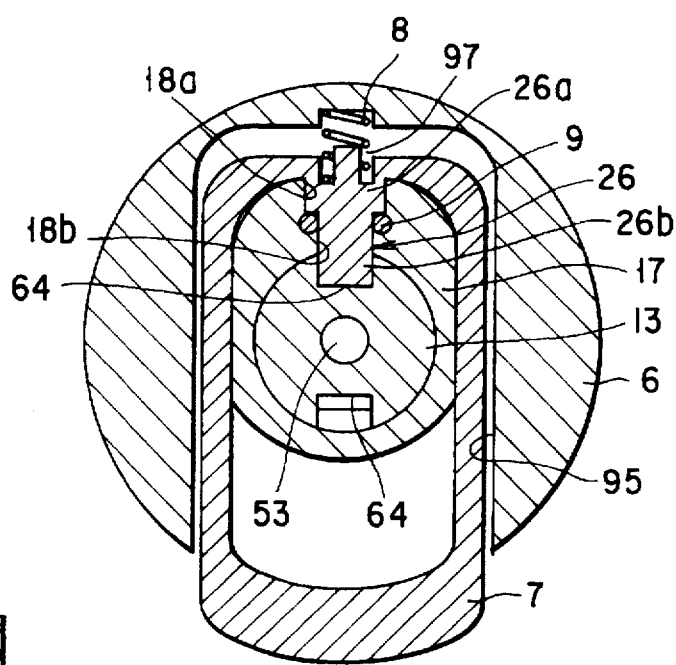
FIG. 10 is a longitudinal sectional view of the release button in an assembled state.

The operating unit proper 5 has a flange 15 at the base end thereof. As shown in FIG. 7, a mount 94 on which a lid member 6 is adapted to be mounted is formed on the base end surface of the flange 15. Engaging grooves 16, 16 for engagement with the lid member 6 are formed respectively at the ends of the mount 94. Also, an engaging member 17 adapted to engage a release button 7 shown in FIG. 8 is protruded from the base end surface of the mount 94. The engaging member 17 has on the outer surface thereof a side hole 18 communicating with the large-diameter portion 12b of the through hole 12 in the same direction as the grooves 16, 16. This side hole 18 includes a large-diameter hole portion 18a and a small-diameter hole portion 18b as shown in FIG. 10. Incidentally, the engaging member 17 is located at the center of the flange 15 coaxially with the operating unit proper 5. A base end opening 11 of the through hole 12 is formed at the base end surface of the engaging member 17. As shown in FIG. 7, the lid member 6 presents a shape of a substantially circular disk, and has an end thereof formed with a groove 95 that can accommodate the mount 94 and the engaging member 17. This groove 95 reaches the peripheral edge of the lid member 6. Also, the lid member 6 has a pair of protrusions 22, 22 protruded inward of the groove 95 in mesh with the grooves 16, 16 of the mount 94. Further, the other end surface of the lid member 6 has formed thereon an opening 21 communicating with the groove 95 and adapted to engage the engaging member 17.

Also, as shown in FIG. 8, the release button 7 includes a rectangular frame 25 adapted to slide in the space formed between the engaging member 17 and the lid member 6 with the operating unit proper 5 and the lid member 6 in an assembled state (the state shown in FIG. 10), and a pin 26 protruded inward of the frame 25. The pin 26 includes a large-diameter portion 26a fitted in the large-diameter hole portion 18a of the side hole 18 of the engaging member 17 and a small-diameter portion 26b fitted in the small-diameter hole portion 18b of the side hole 18. The total length of the pin 26 as assembled on the engaging member 17 is determined in such a manner as to extend a predetermined amount into the large-diameter portion 12b of the through hole 12 of the operating unit proper 5. The amount x of this extension is desirably given by the relation 0 mm<x≦2 mm.

In the case where the lid member 6 is assembled on the operating unit proper 5, as shown in FIG. 10, first, the release button 7 is assembled on the engaging member 17, and an O-ring 9 is interposed between the outer peripheral surface of the small-diameter portion 26b of the pin 26 and the peripheral surface of the large-diameter hole portion 18a of the side hole 18. Next, a spring 8 is loaded in a spring mount hole 97 formed in the bottom of the large-diameter portion 26a of the pin 26. Under this condition, the lid member 6 is fitted in the operating unit proper 5. The fitting procedure will be described below.

First, the protrusions 22, 22 of the lid member 6 are located in the grooves 16, 16 of the operating unit proper 5, and the lid member 6 is then slid from above the operating unit proper 5 along the direction of arrow in FIG. 7. As a result, the grooves 16, 16 come into mesh with the protrusion 22. By the way, in this case, as shown in FIG. 6, the relation L>L' holds between the distance L from the base end surface of the flange 15 to the base end surface of the engaging member 17 and the distance L' from the forward end of the lid member 6 to the forward end of the opening 21 (end surface of the groove 95). The length L is set about 0.5 mm longer than L'. Consequently, this dimensional setting and the facings (bevelings) 23, 24 formed at the starting portion of engagement between the grooves 16, 16 and the protrusion 22 causes the lid member 6 to be progressively deformed while being slid downward of the operating unit proper 5. When the lid member 6 is further slid with respect to the operating unit proper 5 under this condition, the engaging member 17 of the operating unit proper 5 comes to be fitted in the opening 21 of the lid member 6 at the time point when the center of the flange 15 registers with that of the lid member 6. The deformation of the lid member 6 thus is eliminated, so that the protrusions 22, 22 of the lid member 6 come to engage the grooves 16, 16 in longitudinal direction. Also, the engaging member 17 and the opening 21 come to engage each other in diametric direction, and thus the lid member 6 is firmly fixed on the operating unit proper 5.

Under this assembled condition, a minimum play is allowed in all the parts between the operating unit proper 5 and the lid member 6 thereby to prevent any residual stress from being generated due to the assembly work.

Also, with the lid member 6 assembled on the operating unit proper 5 in this way, the release button 7 engaged with the engaging member 17 is partially protruded from the peripheral edge of the lid member 6 through the groove 95, while the spring 8 is held in compressed state between the release button 7 and the lid member 6. This spring 8 biases the release button 7 in such a direction that the forward end of the pin 26 is protruded into the large-diameter portion 12b of the through hole 12. As a consequence, depressing the release button 7 against the biasing force, the pin 26 can be relieved out of the large-diameter portion 12b of the through hole 12. In other words, the pin 26 is prevented from protruding into the large-diameter portion 12b of the through hole 12.

Next, explanation will be made about the first slider 13 and the second slider 36 making up the operating unit 4.

As shown in FIG. 6, the cylindrical first slider 13 is retractively inserted in the through hole 12 of the operating unit proper 5. An operating tube 28 (base-end coil 32) inserted in the lead tube 3 is connected fixedly by brazing or the like means to the forward end of a metal coupling member 59 screwed to the forward end of the first slider 13 by a screw 60 through the forward-end opening 10 of the operating unit proper 5. The reason why this connecting technique is used is that the operating tube 28 is a coil which if fixed by an adhesive would undesirably expand or contract under the force exerted thereon and could undesirably separate the adhesive. Another reason is that the first slider 13 is made of a resin mold and therefore it is impossible to braze the operating tube 28 directly on the first slider 13. Consequently, the operating tube 28 should best be provisionally fixed by brazing or the like method on the metal coupling member 59 and then the screw 60 of the coupling member 59 is bonded by being forced into the first slider 13.

Also, a compression spring 62 is interposed between the screw 60 of the coupling member 59 and the operating unit proper 5. This compression spring 62 is forced into a spiral groove 61 formed in the outer peripheral surface of the coupling member 59 at the forward end of the screw 60. As a result, according to this configuration, an adhesive is coated also on the compression spring 62 arranged in the spiral groove 61 at the time of the forced-in bonding of the first slider 13 and the coupling member 59, so that bonding work can be performed at the same time between the compression spring 62 and the coupling member 59 on the one hand and between the coupling member 59 and the first slider 13 on the other hand.

Two guide grooves 64, 64 are arranged along the length on the outer peripheral surface at the forward end side of the first slider 13. These two guide grooves 64, 64 are disposed at an angular interval of 180 degrees to each other along the peripheral direction. Each guide groove 64 has a width slightly larger than the diameter of the small-diameter portion 26b of the pin 26 of the release button 7 mounted on the operating unit proper 5. The forward end side of the guide groove 64 forms a shallow first guide groove portion 64a, and the base end side thereof constitutes a deep second guide groove portion 64b on both sides of a midway step 99 as a boundary. In this configuration, the pin 26 of the release button 7 is located at the forward end of the first guide groove portion 64a and also at the forward end of the second guide groove portion 64b of one guide groove 64, thereby restricting the amount by which the operating tube 28 is pulled into the lead tube 3 while at the same time restricting the rotation of the first slider 13.

By the way, the compression spring 62 is dimensionally set in such a manner as to hold the compression force between the operating unit proper 5 and the first slider 13 when the pin 26 is placed in the second guide groove portion 64b on the second step and also to release the compression force when the pin 26 is located at the forward end of the first guide groove portion 64a on the first step.

Also, with the pin 26 located on the second guide groove portion 64b, the operating tube 28 is protruded from the forward-end opening of the lead tube 3. If the pin 26 is retracted into the side hole 18 of the operating unit proper 5 by depressing the release button 7 under this condition, the pin 26 disengages from the second guide groove portion 64b so that the biasing force of the compression spring 62 automatically retracts the operating tube 28 into the lead tube 3.

By the way, two guide grooves 64 are provided on the first slider 13 by reason of the fact that while the protrusion 7a of the release button 7 and the pin 26 are structurally located in opposite positions separate by 180 degrees from each other, the user may misunderstand that the pin 26 is located on the protrusion 7a of the release button 7 and thus may erroneously dispose the first slider 13 at a position 180° opposite with respect to the operating unit proper 5.

Also, as shown in FIG. 2, a first slit 56 is formed along the longitudinal direction on the base end side of the first slider 13. Further, an expansion 13a expanding substantially perpendicular to the length of the first slider 13 from the two sides of the first slider 13 is formed at the forward end side of the first slit 56. This expansion 13a is formed with a second slit 57 perpendicular to the first slit 56. The second slider 36 is mounted movably along the first slit 56, and a rotative operation member 55 fixed as described later on the base end side of the operating wire 33 is arranged rotatably in the second slit 57. This configuration will be described in more detail with reference to FIG. 6.

As shown in FIG. 6, the operating wire 33 extends from the base end opening of the operating tube 28 fixedly connected at the forward end of the coupling member 59. This extended operating wire 33 is rotatably coupled to the second slider 36. Also, a plurality of tubular members 34, 53 are fitted to cover the outer peripheral portion of the operating wire 33 extending from the base end opening of the operating tube 28.

Figure 11:
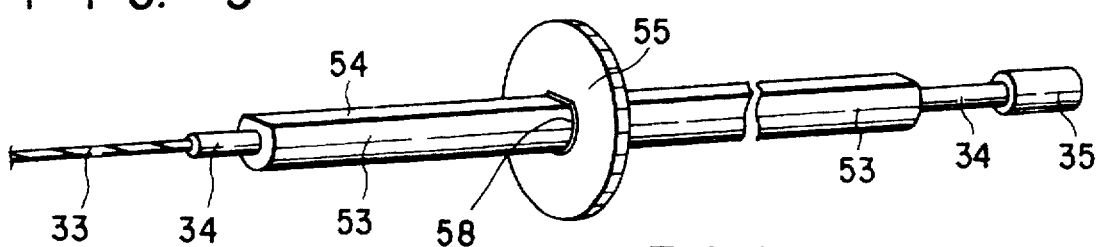
FIG. 11 is a perspective view showing a configuration of the base end of the operating wire.

In other words, as shown in FIG. 11, in order to prevent the operating wire 33 from buckling in the neighborhood of the second slider 36, an operating pipe 34 made of a pipe material such as stainless steel is fitted to cover the outer periphery of the extension of the operating wire 33. Further, a cylindrical wire support 35 made of stainless steel or the like material is fitted to cover the outer periphery of the base end of the operating wire 34.

Figure 9:
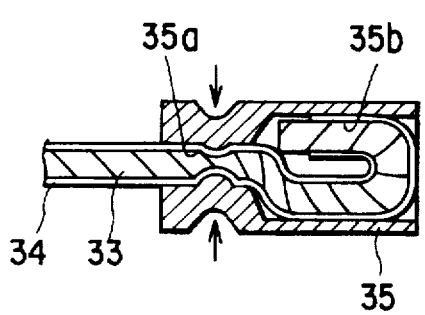
FIG. 9 is a longitudinal sectional view showing the operating wire in coupled state with a wire support.

As shown in FIG. 9, the wire support 35 has a small-diameter hole 35a into which the operating pipe 34 can be inserted and a large-diameter hole 35b larger than the small-diameter hole 35a. The operating pipe 34, together with the operating wire 33 inserted into it, is led to the large-diameter hole 35b through the small-diameter hole 35a of the wire support 35, and is folded back together with the operating wire 33 in the large-diameter hole 35b. By caulking the outer peripheral portion where the small-diameter hole 35a of the wire support 35 is located, the wire support 35, the operating pipe 34 and the operating wire 33 are integrally fixed.

By the way, this fixing operation can of course be performed also by soldering. The use of soldering, however, may corrode off the operating wire 33 due to the residual flux or the like. Also, many other problems are posed since such operations are required as the filing for removing extraneous solder and the cleaning process for removing flux. Taking these points into consideration, therefore, the fixing work by caulking is said to be preferable after all.

Also, as shown in FIG. 11, a rotating pipe 53 is fitted to cover the outer periphery of the operating pipe 34 in spaced relationship with the wire support 35. This rotating pipe 53 is made of a pipe material such as brass and has a flat portion 54 over the substantially entire length thereof. In other words, this rotating pipe 53 has a D-shaped section. Also, a disk-shaped rotative operation member 55 is slidably fitted on the outer periphery of the rotating pipe 53. In this case, a D-shaped through hole 58 having the same sectional shape as the rotating pipe 53 is formed at the central portion of the rotative operation member 55 to permit the turning effort of the rotative operation member 55 to be transmitted to the rotating pipe 53 (hence, also to the operating wire 33). Therefore, the rotative operation member 55 cannot rotate with respect to the rotating member 53. By the way, in the case where the section of the rotating pipe 53 is not D-shaped but is a rectangle or hexagon, by contrast, the shape of the through hole 58 of the rotative operation member 55 of course also assumes a rectangular or hexagonal shape, as the case may be.

Also, nickel, chromium or the like is plated on the surface of the rotating pipe 53. The rotating pipe 53 is fixed on the operating pipe 34 by caulking the base end thereof. Of course, the fixing between the rotating pipe 53 and the operating pipe 34 may alternatively be accomplished by brazing or the like.

The base end side of the operating wire 33 configured by being covered with the operating pipe 34 and the rotating pipe 53 in the above-mentioned manner is projected into the first slit 56 by being retractively inserted into the inner hole 120 of the first slider 13. This base end is fixed on the second slider 36, which is movable along the first slit 56, through the wire support 35. Also, the rotative operation member 55 fitted on the outer periphery of the rotating pipe 53 is arranged in the second slit 57 formed in the expansion 13a of the first slider 53. The rotative operation member 55 is fitted slidably (but not rotatably as described above) on the outer periphery of the rotating pipe 53, and therefore the turning effort of the rotative operation member 55 can be transmitted to the rotating pipe 53 in any state of retraction of the rotating pipe 53. This turning effort is transmitted from the rotative operation member 55 to the rotating pipe 53 to the operating pipe 34 to the operating wire 33 to the hook 30 to the cassette-type clip 2. In other words, by rotating the rotative operation member 55 with the clip device led into the body cavity by way of the endoscope, the direction in which the clip 45 of the cassette-type clip 2 is opened can be remotely controlled from outside the body.

As shown in FIG. 6, the rotative operation member 55 is arranged forward of the area where the second slide 36 slides. This is intended to facilitate the operation on the assumption that the second slider 36 is manipulated by the right hand and rotated by the left hand.

As shown in FIG. 6, the second slider 36 mainly includes two holding members 65, 65 for holding and fixing the wire support 35 mounted at the base end of the operating wire 33, and a cover member 122 for integrally covering the holding members 65, 65 from outside.

Two holding members 65, 65 are used as the same members in order to decrease the product cost. Each holding member 65 includes a tabular sliding section 65a slidable in the first slit 56 of the first slider 13 and a semicircular section 65b located at the base end side of the sliding section 65a. A notch 69 is formed in each sliding section 65a. The two holding members 65, 65 are coupled in such a position that the two notches thereof are in opposed relation to each other. At the same time, the wire support 35 is arranged in the closed space formed by the two notches 69, 69. The operating wire 33 thus can be rotatably fixed on the second slider 36 through the wire support 35.

The sliding section 65a has a relief 70 cut at the forward end thereof, and also has a pawl 71 protruded from the outer surface of the forward end thereof. The cover member 122 and the two holding members 65, 65 are fixed by pressing the coupled pair of the holding members 65, 65 into the inner hole 122a of the cover member 122 from the base end side of the cover member 122. In the process, the pawl 71 of the holding member 65, 65 is pressed in along a groove 72 (see FIG. 13) formed in the inner hole 122a of the cover member 122. This pressing operation is performed by taking advantage of the fact that the forward end of the sliding section 65a is displaced by the relief 70. When the holding members 65, 65 and the cover member 122 come to a predetermined position, the pawl 71 is caught in an engaging section 73 formed at the forward end of the cover member 122, so that the two component parts are fixed on each other.

The semicircular portion 65b of the holding member 65 is formed with a rectangular through hole 75 passing through the semicircular portion 65b in the perpendicular direction from the semicircular flat portion 74. This through hole 75 has arranged slidably therein a ratchet release button 68, an engaging means 66 and a spring 67. The spring 67 is arranged in a state compressed between the engaging means 66 and the inner wall of the second slider 36. The spring 67 causes the engaging means 66 to be pressed against the engaging pawl 76 of the first slider 13, thereby restricting the movement of the second slider 36 toward the forward end of the first slider 13. In other words, the engaging means 66 and the engaging pawl 76 constitute a ratchet mechanism. The ratchet release button 68 is passed through the through hole 75 and the through hole 77 of the cover member 122 communicating with the through hole 75. Upon depression of the ratchet release button 68, the engaging means 66 is pushed up and releases the engagement between the engaging means 66 and the engaging pawl 76.

Also, the clearance between the through hole 75 and the bar-shaped sliding section 68a at the forward end of the ratchet release button 68 located in the first slit 56 is desirably about 0.01 to 0.2 mm. This is by reason of the fact described below.

Specifically, in this clip device, as described later, the J-shaped hook 51 of the cassette-type clip 2 is extended by pulling the second slider 36 toward the operator, and in this way the cassette-type clip 2 and the clip device proper 1 are separated from each other thereby to retain the cassette-type clip 2 in the affected part. In the process, the force thus far exerted on the second slider 36 is released, so that the second slider 36 abruptly moves toward the operator with the result that the base end of the second slider 36 and the base end of the first slit 56 of the first slider 13 come to strike violently each other. If a large clearance is allowed between the sliding section 68a of the ratchet release button 68 and the through hole 75, on the other hand, the base end of the holding members 65, 65 is undesirably subjected to plastic deformation, and the through hole 75 is crushed, thus preventing the engaging means 66 and the sliding section 68a of the ratchet release button 68 from smooth sliding. In order to prevent such a troublesome situation, the clearance between the sliding section 68a and the through hole 75 is minimized to eliminate the space which otherwise might be available for the plastic deformation of the holding members 65, 65. Even in the case of a violet collision, the holding members 65, 65 thus absorb the impact by elastic deformation, thereby permitting the engaging means 66 and the sliding section 68a of the ratchet release button 68 to smoothly slide. Also, the two holding members 65, 65 are surrounded by the cylindrical cover member 122 to prevent the holding members 65, 65 from being dislocated due to the collision.

Figure 12:
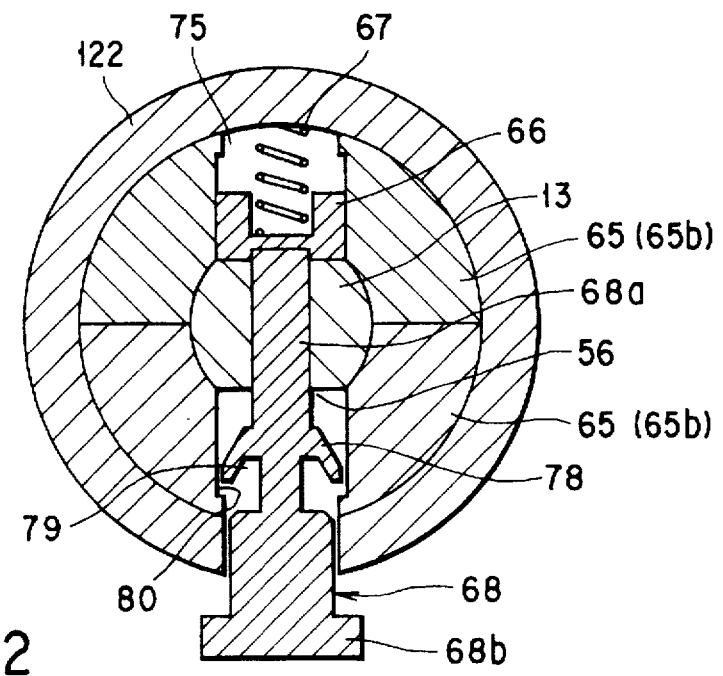
FIG. 12 is a longitudinal sectional view of a ratchet release button in an assembled state.
Figure 13:
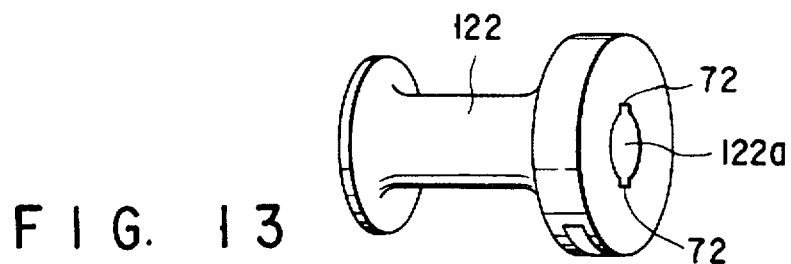
FIG. 13 is a perspective view showing a cover member of a second slider.

By the way, as shown in FIG. 12, the ratchet release button 68 includes a stopper 78 adapted to expand toward the button 68b. By displacing the space 79 inside the stopper 78, the ratchet release button 68 can be fitted in the through hole 75 of the holding members 65, 65. Also, the ratchet release button 68, after being thus fitted, is prevented from coming off as the stopper 78 engages the step 80 of the through hole 75.

By the way, as shown in FIG. 6, an annular handle 105 is provided at the base end of the first slider 13.

Next, the operation of the clip device configured as described above will be explained. First, the first slider 13 of the operating unit 4 is pushed out toward the forward end thereof, whereby the pin 26 is located in the second guide groove portion 64b of the first slider 13 thereby to project the operating tube 28 from the lead tube 3. Under this condition, the cassette-type clip unit 2 is mounted on the hook 30 on the side of the clip device proper 1.

For mounting this clip unit 2, the second slider 36 of the operating unit 4 is slid toward the forward end thereof and the hook 30 at the forward end of the operating wire 33 is projected outside of the operating tube 28. Next, a head 42a of the pin 42 of the hook 3 is fitted in the large-diameter hole 52b of the coupling plate 37 of the clip unit 2, and under this condition the clip unit 2 is pulled toward the forward end.

Then, the slot portion 52a of the engaging hole 52 of the coupling plate 37 is fitted on the neck 42b of the pin 42 of the hook 30, and thus is settled in position not to easily come off. Under this condition, the second slider 36 of the operating unit 4 is pulled toward the operator, and the hook 30 is retracted into the coupling ring 29 through the operating wire 33. The coupler 46a of the clip-fastening ring 46 on the side of the cassette-type clip unit 2 is fixedly fitted in the coupling ring 29. As a result, the cassette-type clip unit 2 is loaded in the clip device proper 1.

Next, the first slider 13 of the operating unit 4 is slid toward the operator and thus the operating tube 28 is pulled into the lead tube 3. The operating tube 28 thus is accommodated in the lead tube 3 with the clip 45 closed. The operating tube 28, together with the lead tube 3, is thus led into the vital body cavity through the endoscope channel, after which the first slider 13 of the operating unit 4 is pushed out toward the forward end. The operating tube 28 thus pushed out of the lead tube 3, thereby projecting the clip 45 out of the lead tube 3. In the process, the arms 49a, 49b of the clip 45, which have the inherent tendency of widening open, open widely.

Figure 14:
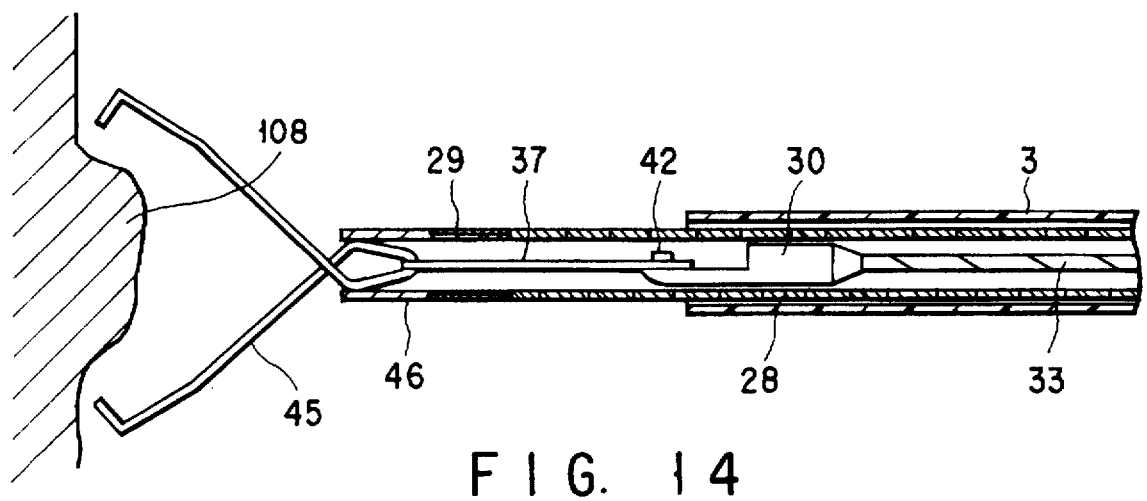
FIG. 14 is a sectional view showing the manner in which the tissue is bound using a clip device.

After that, the second slider 36 of the operating unit 4 is pulled toward the operator, and the hook 30 thus is also pulled toward the operator through the operating wire 33. As a consequence, the loosely-fitted portions 48a, 48b of the clip 45 are retracted into the clip-fastening ring 46. Then, as shown in FIG. 14, the loosely-fitted portions 48a, 48b are crushed, with the result that the arms 49a, 49b of the clip 45 open to the widest degree. With the arms 49a, 49b of the clip 45 open widest this way, the rotative operation member 55 is rotated in an arbitrary direction thereby to orient the clip 45 in the desired leg-open direction. If the second slider 36 is returned several ratchets toward the forward end in advance, the operating wire 33 can be more smoothly rotated by the rotative operation member 55. This is by reason of the fact that the operating wire 33 is tensioned in order to open wide the clip 45, and with the friction resistance between the clip unit 2 and the coupling ring 29 increased by this tension, the operating wire 33 is fixed by ratchet. By returning the second slider 36 several ratchets toward the forward end, however, the tension can be released.

After the leg-open direction of the cassette-type clip 2 is set in an optimum direction by this operation, the clip 45 is pressed against the vital tissue 108 requiring the clipping operation. The second slider 36 is pulled toward the operator again, and the operating wire 33 thus pulled also toward the operator. Then the arms 49a, 49b of the clip 45 strike the clip-fastening ring 46, and further are pulled into the clip-fastening ring 46, so that the arms 49a, 49b of the clip 45 are closed and the holders 50a, 50b hold the vital tissue 108 tightly between them.

Pulling the operating wire 33 further toward the operator, the clip 45 is struck deep into the vital tissue 108 as shown in FIG. 15A. At the same time, the hook 51 of the coupling plate 37 is extended as shown FIGS. 15B and 15C and the clip 45 comes off from the coupling plate 37. By the way, the clip-fastening ring 46, which presses the arms 49a, 49b of the clip 45, does not come off from the clip 45 as shown in FIG. 15A and is retained in the body together with the clip 45.

As described above, with the clip device according to this embodiment, the forward-end treatment section can be rotated without adversely affecting the mechanisms for other than the rotation. Further, rotation can be accomplished in both directions securely without any skip or similar irregularities. As a result, the clipping work is done easily.

Figure 16:
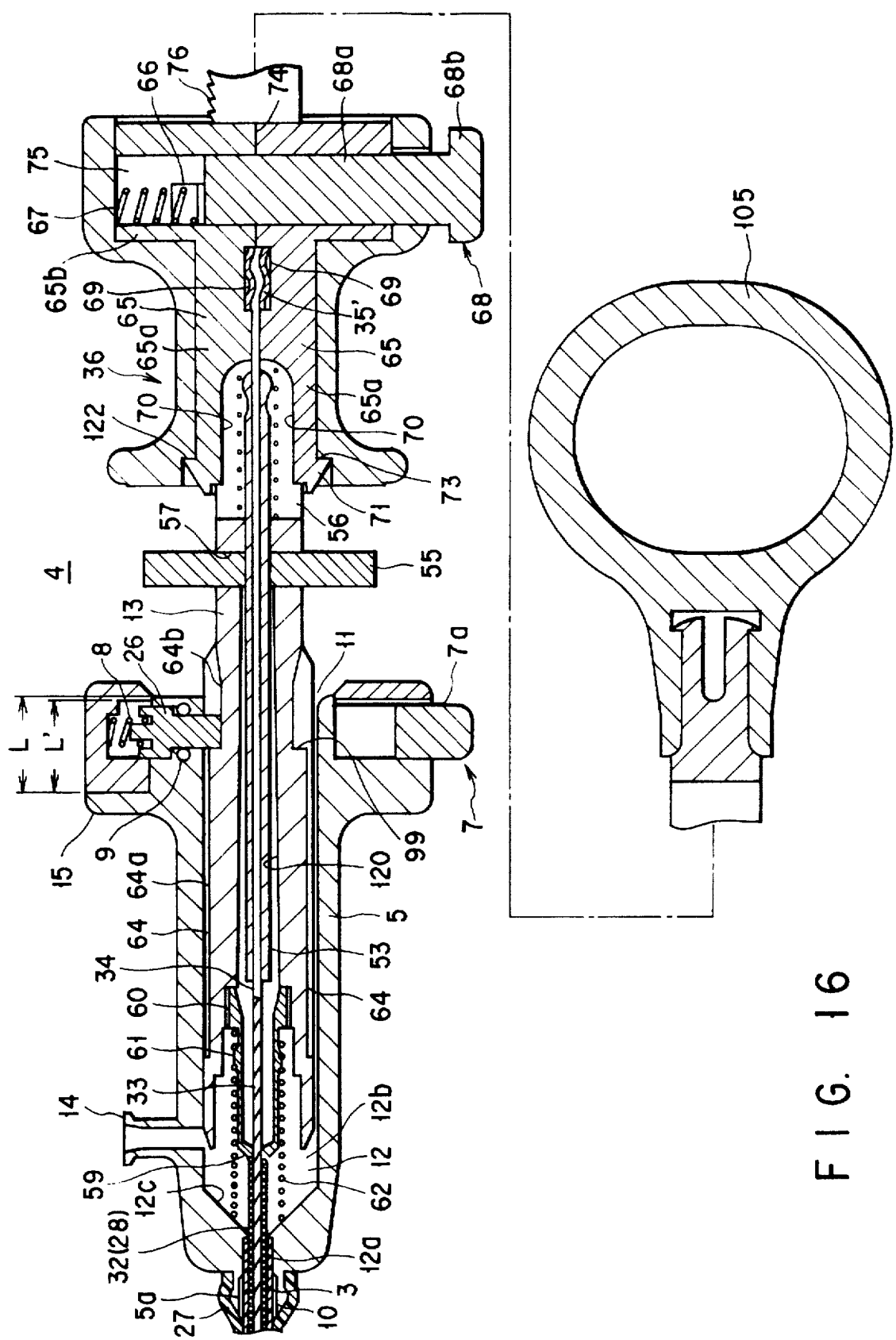
FIG. 16 is a sectional view showing an operating unit of a clip device according to a second embodiment of the invention.
Figure 20A:
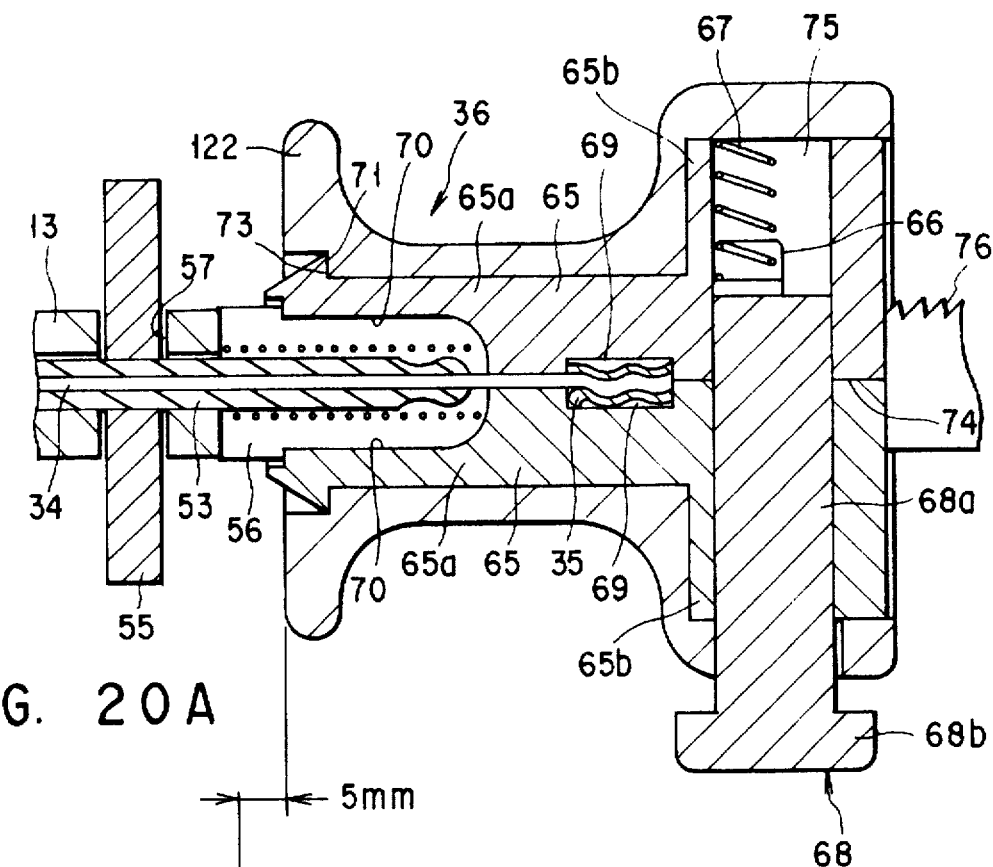
FIGS. 20A and 20B are sectional views of a second slider.
Figure 20B:
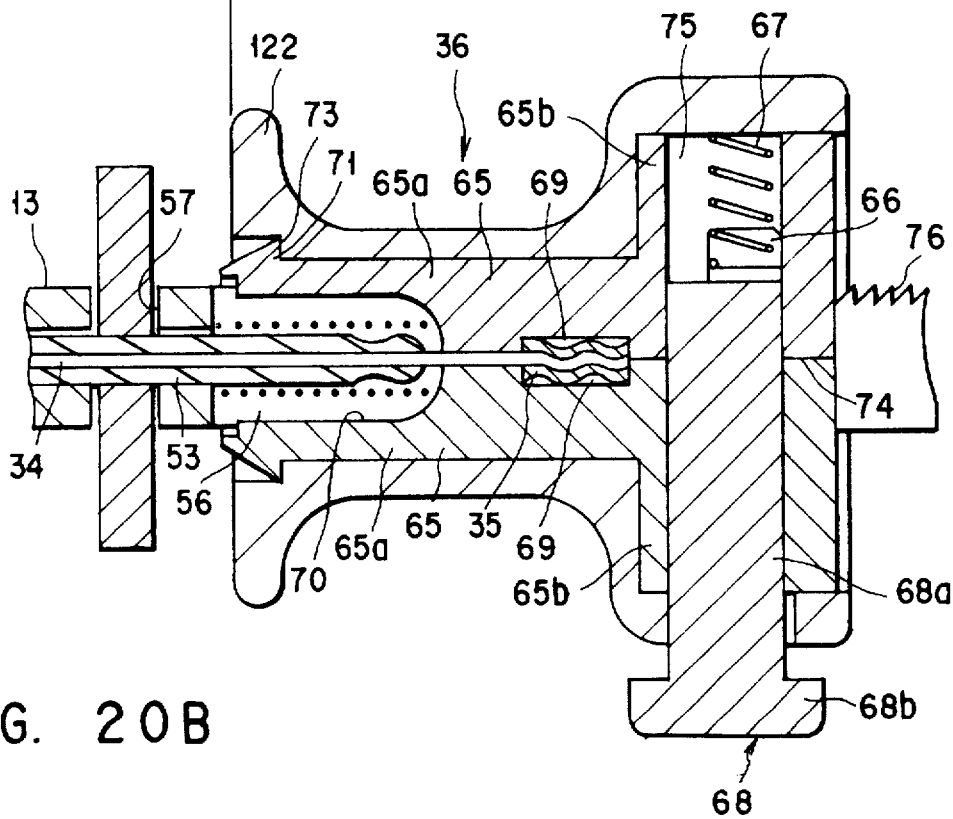

FIGS. 16 to 20 show a second embodiment of the invention. As shown in FIG. 16, according to this embodiment, the only difference from the first embodiment lies in the construction of the second slider and the fixed state of the base end of the wire 33, while the other configurations are identical to those of the first embodiment.

More specifically, as shown in FIG. 16, the length of the engaging means 66 along the length of the first and second sliders 13, 36 is shorter by about 5 mm than the length of the through hole 75 along the length of the first and second sliders 13, 36. Even with the ratchet mechanism turned on, therefore, the second slider 36 is adapted to move by about 3 to 10 mm, or preferably, by about 5 mm, with respect to the first slider 13.

Also, a cylindrical wire support 35' made of stainless steel or the like material is fitted on the outer periphery of the base end of the operating pipe 34 in which the operating wire 33 is inserted. Under this condition, the outer periphery of the wire support 35' is caulked as shown in FIGS. 17 and 18, thereby integrally fixing the wire support 35', the operating pipe 34 and the operating wire 33.

The fixedly-caulking operation is accomplished by a caulking device having a caulking section 102 as shown in FIG. 19. The caulking section 102 includes a recessed support 100 and a protruded portion 101. The side of the wire support 35' is held between the support 100 and the protruded portion 101 to perform the caulking work. Under a caulked condition, as shown in the longitudinal sectional view of FIG. 17, the operating wire 33 and the operating pipe 34 are sided to the support 100 of the caulking section 102. As shown in FIG. 18, the caulking process is effected at two pints on the side displaced in the longitudinal direction of the wire support 35'. The caulking operation at the two points is carried out with the caulking section 102 oriented in different directions. In other words, as shown in FIG. 18, the caulking work at the two points increases the strength of securing the operating pipe 34 and the operating wire 33 to each other by means of a corrugation formed thereon. Also, in the case where the outer diameter of the wire support 35' is 2 mm and the outer diameter of the operating pipe 34 about 0.8 mm, the distance between the two caulking points 91, 91 is desirably about 0.5 mm. This is because an excessively short interval between the two caulking points 91, 91 would cause an excessively bent condition of the operating pipe 34, which in turn would lead to a breakage initiated at the bent part. In the case where the corrugation pitch of the operating pipe 34 and the operating wire 33 is too long, on the other hand, the fixing strength fails to reach a sufficiently high level. By the way, the caulking operation may of course be performed at three or more points. In this case, too, however, adjacent caulking points 91, 91 are required to be caulked in opposite directions.

With the configuration according to this embodiment, when the rotative operation member 55 is rotated in an arbitrary direction with the arms 49a, 49b of the clip 45 open to the widest degree in order to open the legs of the clip 45 in the desired direction, the second slider 36 is moved about 3 to 10 mm, or preferably about 5 mm, toward the forward end. In this way, the rotative operation member 55 (the operating wire 33) can be more smoothly rotated. This is due to the fact that the tension imposed on the operating wire 33 for opening the legs of the clip 45 (the state shown in FIG. 20A) can be released by moving the second slider 36 by about 3 to 10 mm or preferably by about 5 mm toward the forward end (the state shown in FIG. 20B). Also, this movement of 3 to 10 mm or preferably about 5 mm can be accomplished with the ratchet mechanism turned on.

As described above, according to this embodiment, the same effect of operation can be obtained as the first embodiment. At the same time, the second slider 36 can be moved by about 3 to 10 mm or preferably by about 5 mm toward the forward end without releasing the ratchet before rotation. The tension exerted on the wire thus can be released safely and securely, thus permitting a smoother rotation.

Further, since the wire support 35 is caulked in such a manner that the operating pipe 34 and the operating wire 33 are corrugated appropriately, a low-cost fixing arrangement is possible with a high fixing strength.

Figure 21:
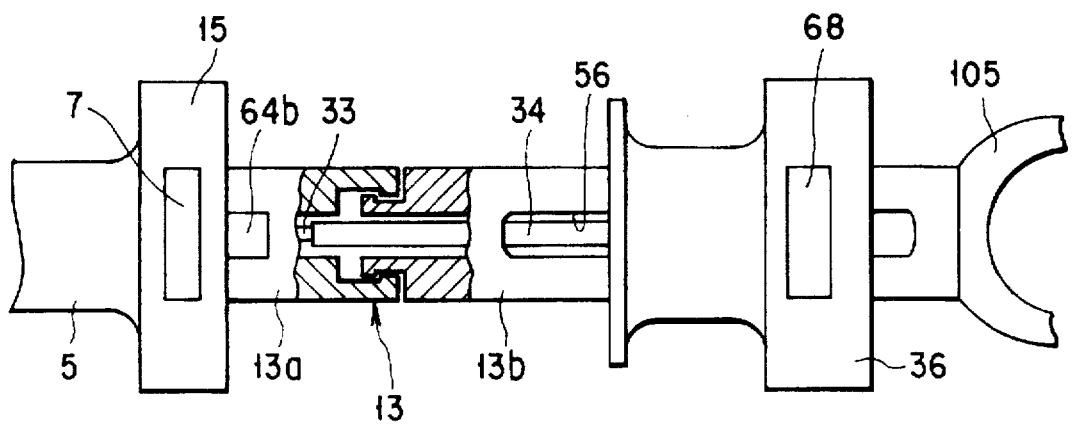
FIG. 21 is a longitudinal side sectional view showing a coupling structure of the operating unit of a clip device according to a third embodiment of the invention.

FIG. 21 shows a third embodiment of the invention. This embodiment is different from the first embodiment in that the first slider 13 is split into two parts at the base end side of the second guide slot 64b.

More specifically, the first slider 13 includes a forward-end slider portion 13a adapted to slide in the operating unit proper 5 and connected to the operating tube 28 and a base-side slider portion 13b having a first slit 56 and rotatably coupled to the forward-end slider portion 13a. Also, the operating wire 33 is rotatably connected to the second slider 36 together with the operating pipe 34 fitted to cover the outer periphery thereof. As a consequence, unlike the configuration of the first embodiment, the present embodiment does not include the rotating pipe 53, the rotative operation member 55 and the second slit 57. The other configuration of the embodiment is identical to that of the first embodiment.

In this configuration of the present embodiment, rotation of the base-end slider portion 13b with the forward-end slider portion 13a held appropriately can rotate the cassette-type clip unit 2.

Figure 22:
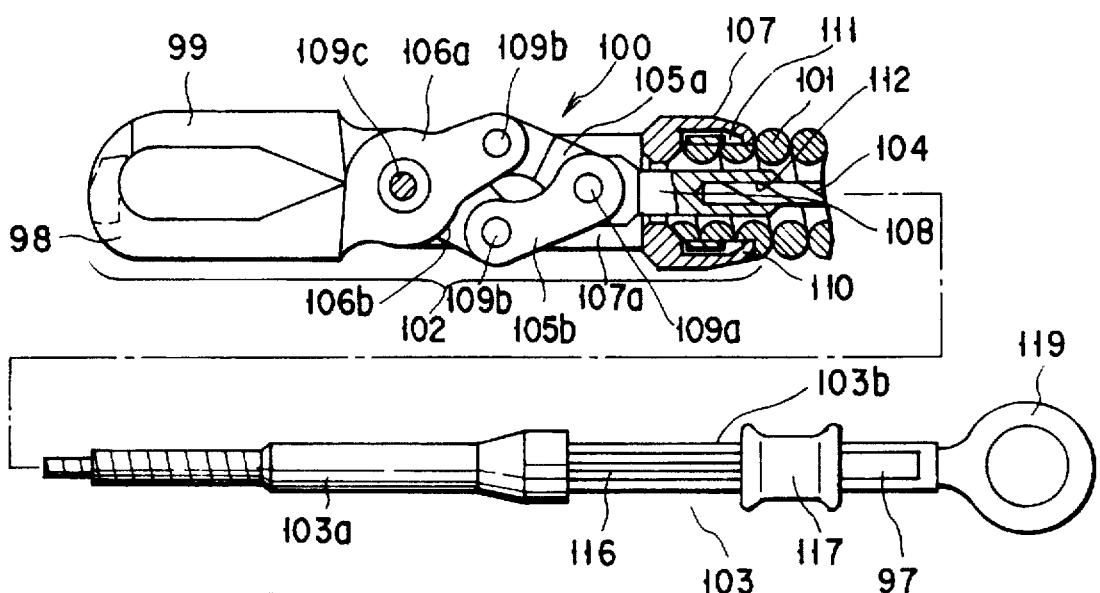
FIG. 22 is a partially cutaway side view showing a general configuration of a holding clamp according to a fourth embodiment of the invention.
Figure 23:
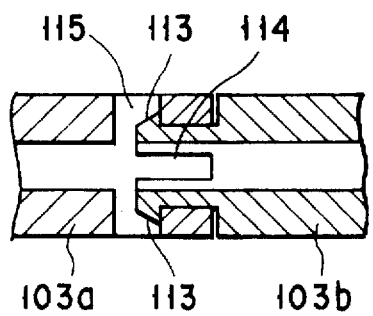
FIG. 23 is a longitudinal side sectional view showing a coupling structure of the operating unit of the holding clamp shown in FIG. 22.
Figure 24:
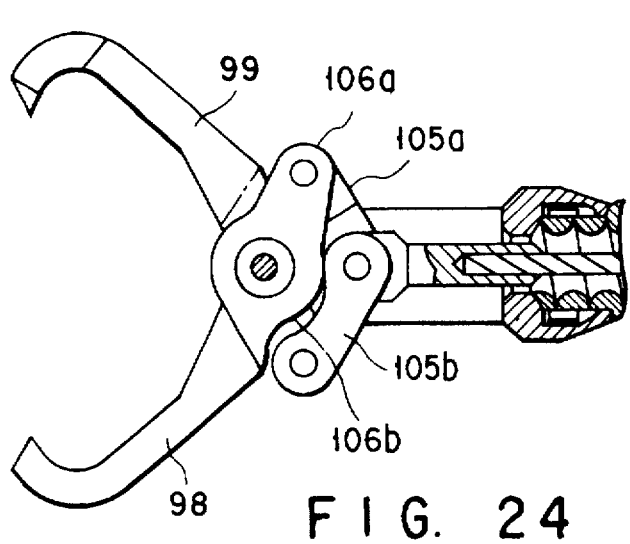
FIG. 24 is an enlarged view showing the treatment section of the holding clamp in open state.

FIGS. 22 to 24 show a fourth embodiment of the invention. According to the present embodiment, a holding clamp is shown as an endoscopic treatment tool.

As shown in FIGS. 22 and 23, the holding clamp 100 includes a sheath 101 having a densely-wound flexible coil, a treatment section 102 formed at the forward end of the sheath 101, and an operating unit 103 provided on the operator's side of the sheath 101. An operating wire 104 having a torque transmissivity for transmitting the motion of the operating unit 103 to the treatment section 102 is inserted in the sheath 101. A coupling member 108 is fixed at the forward end of the operating wire 104. The coupling member 108 and the operating wire 104 are fixed by brazing with the operating wire 104 inserted into the fixing hole 112 formed at the base end of the coupling member 108.

Also, the coupling member 108 has rotatably mounted thereon a pair of first links 105a, 105b through a pin 109a. Second links 106a, 106b are rotatably mounted on the ends of the first links 105a, 105b respectively through a pin 109b. By the way, the second links 106a, 106b have formed at the ends thereof holders 98, 99 respectively. By means of a link mechanism configured by mounting the second links 106a, 106b rotatably relative to each other through a pin 109c, the retracting operation of the operating wire 104 is converted into the open-close operation of the holders 98, 99.

The links 105a, 105b, 106a, 106b making up the link mechanism are arranged in the slit 107a of the forward-end member 107 connected to the forward end of the sheath 101. The forward-end member 107 has a slot 111 at the base end thereof. While an annular engaging member 110 mounted at the forward end of the sheath 101 is engaged with the slot 111, the base end of the forward-end member 107 is caulked over the entire periphery thereof, thereby rotatably fixing the forward-end member 107 and the sheath 101. By the way, the slot 111 is formed with a diameter slightly larger than the outer diameter of the engaging member 110 and with a length slightly longer than the engaging member 110.

The operating unit 103 includes a forward-end side operating unit portion 103a and a base-end side operating unit portion 103b. As shown in FIG. 23, at least one pawl 113 is formed at each of two peripherally opposite points on the forward end of the base-end operating unit portion 103b. A slit 114 into which the pawls 113 are adapted to be displaced inwardly to each other is formed between the pawls 113. Also, a plurality of engaging holes 115 adapted to engage the pawl 113 are formed in a predetermined length along the peripheral direction at the base end of the forward-end operating unit portion 103a. With this configuration, therefore, once the inwardly-displaced pawl 113 is caused to engage the engaging hole 115 of the forward-end operating unit portion 103a, the forward-end operating unit portion 103a and the base-end operating unit portion 103b are allowed to be rotatably coupled to each other.

Also, the base-end operating unit portion 103b has a slit 97 for guiding the slider 117 in a retractive way. The slider 117 is connected with an operating wire 117 through an operating pipe 116. In this case, the operating wire 104 is connected to the slider 117 in an unrotatable manner by adhesive or the like.

Now, the operation of the present embodiment will be explained.

First, the holding clamp 100 having the above-mentioned configuration is inserted into the channel of the endoscope not shown, and is led to the part to be treated in the body cavity through the channel. Next, the treatment section 102 is brought near to the part to be treated in the body cavity by being projected from the forward end of the endoscope. The thumb is inserted into the finger ring 119 of the base-end operating unit portion 103b, while the slider 117 is held between the forefinger and the middle finger of the same hand thereby to slide the slider 117 back and forth along the slit 97. As a result, the operating wire 104 is pushed and pulled along the axial direction in the sheath 101, so that the holders 98, 99 of the treatment section 102 are opened and closed through the link mechanism described above. More specifically, when the operating wire 104 is pulled by sliding the slider 117 toward the operator, the holders 98, 99 are closed, whereas the holders 98, 99 are opened when the slider 117 is slid forward to push out the operating wire 104.

Assume that the forward-end operating unit portion 103a is held and the whole of the base-end operating unit portion 103b is rotated with the holders 98, 99 open as shown in FIG. 24, then the whole treatment section 102 is rotated through the operating wire 104, so that the opening direction of the holders 98, 99 can be changed in a desired direction. When the holders 98, 99 are closed from a state open in the desired direction, therefore, foreign matters in the body cavity can be held and the tissue biopsy can be performed accurately.

Figure 25:
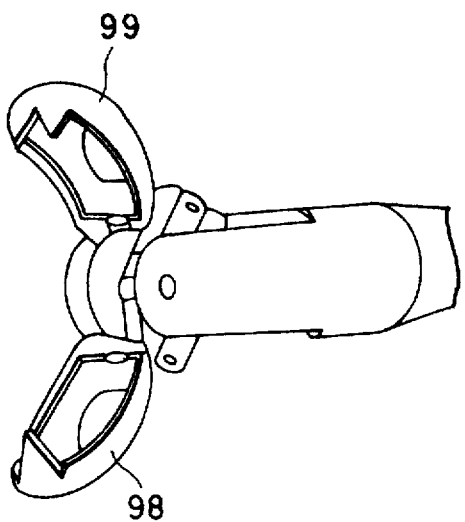
FIG. 25 is a perspective view showing a configuration of the treatment section of the holding clamp formed in cup shape.

By the way, the holders 98, 99 may be cup-shaped as shown in FIG. 25.

Figure 26:
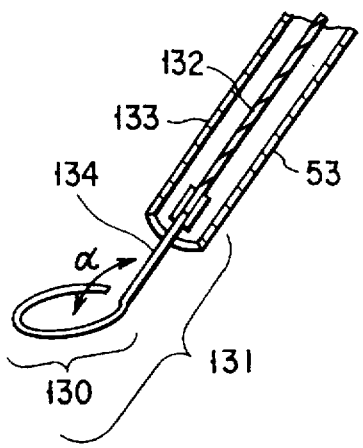
FIG. 26 is a perspective sectional view showing the essential parts of a high-frequency marking device according to a fifth embodiment of the invention.

FIG. 26 shows a fifth embodiment of the invention. According to this embodiment, a high-frequency marking device is shown as an endoscopic treatment tool. As shown, the high-frequency marking device includes a marking section 131 constituting a ring section 130, an operating wire 132 having a torque transmissivity connected to the base end of the marking section 131, and a tube sheath 133 into which the operating wire 132 is adapted to be inserted. The marking section 131 includes a shape memory alloy for storing the annular shape of the ring 130 and the angle α that the axis 134 extending from the root of the ring section 130 forms to the ring section 130. By extending linearly the ring section 130 which can be extended so, the marking section 131 is adapted to be retracted into the tube sheath 133.

A water cock (not shown) is mounted on the base end of the tube sheath 133. Also, an operating unit not shown is arranged on the base end of the tube sheath 133. The operating unit is connected electrically with a high-frequency device for supplying high frequencies to the marking section 131 through the operating wire 132. Also, the operating unit is configured as described in any one of the first to fourth embodiments, whereby the operating wire 132 can be rotated while being advanced or retracted.

In the case where a treatment is carried out using a high-frequency marking device configured this way, first, the marking device 131 is extended linearly into the tube sheath 133, and the tube sheath 133 is then led into the body cavity by way of endoscope. The marking section 131 is projected from the tube sheath 133 by operating the operating unit, while at the same time supplying warm water to the marking section 131 through the inner hole of the tube sheath 133. The heat of the warm water causes the marking section 131 to restore the memorized shape thereof. In other words, the ring section 130 is formed and the angle α is formed between the ring section 130 and the axis 134.

Next, the operating wire 132 is rotated and the marking section 131 is oriented in the desired direction. Under this condition, the ring section 130 is pressed against the tissue. A high-frequency current is supplied to the marking section 131 through the operating wire 132 thereby to attach an annular marking on the tissue.

As described above, according to this embodiment, the surface of the ring section 130 can be oriented in the optimum direction with respect to the tissue to be marked, and therefore a marking can be accomplished with high accuracy.

Figure 27:
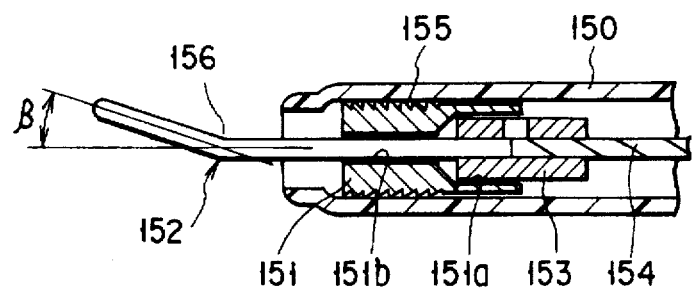
FIG. 27 is a longitudinal side sectional view showing the forward end of a high-frequency incision tool according to a sixth embodiment of the invention.

FIG. 27 shows a sixth embodiment of the invention. According to this embodiment, a high-frequency incision device of precutting type is shown as an endoscopic treatment tool.

As shown, the high-frequency incision tool includes a sheath 150 made of a flexible tube, an engaging member 151 pneumatically forced into the forward end of the sheath 150, a knife 152 in the shape of a round rod adapted to be projected or retracted from the sheath 150 through the inner holes 151a, 151b of the engaging member 151 and elastically bent in the direction at an angle β to the axis of the sheath 150, and an operating wire 154 having a torque transmissivity mounted through a connecting pipe 153 on the base end of the knife 152.

The engaging member 151 is firmly secured to the sheath 150 by an engaging member 155 with a saw-toothed section formed around the outer periphery of the engaging member 151. The inner hole of the engaging member 151 includes a large-diameter hole portion 151a and a small-diameter hole portion 151b. The small-diameter hole portion 151b has the diameter thereof set in such a manner that the knife 152 can be slidably inserted into it while the connecting pipe 153 cannot be inserted into it. The large-diameter hole portion 151a, on the other hand, has the diameter thereof set in such a manner that the connecting pipe 153 can be inserted into it.

A bent portion 156 of the knife 152 bent in the direction at an angle β to the axial direction of the sheath 150 is located in such a position that the forward end of the connecting pipe 153 is projected from the small-diameter hole portion 151b while being butted in contact with the forward end of the large-diameter hole portion 151a.

Though not shown, the operating wire 154 is advanced or retracted while being rotatively operated by the same operating mechanism as in any one of the first to fourth embodiments.

In the case where the duodenum papilla is precut using the high-frequency incision tool configured as described above, the high-frequency incision tool is inserted into the channel of the endoscope not shown and led to the part to be treated in the body cavity through the channel. The operating wire 154 is rotated from the operator's side by means of an operating mechanism to orient the knife 152 in an optimum direction to incise the duodenum papilla. By the way, the precutting method is well-known and therefore will not be described again.

As described above, according to this embodiment, the knife 152 can be oriented in the desired direction, and therefore a situation can be avoided in which hemorrhage is caused as the duodenum papilla is cut in an erroneous direction, thereby making possible a safe precutting operation.

Figure 28:
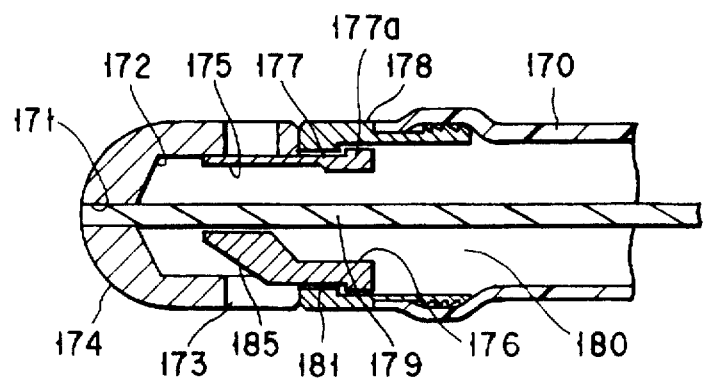
FIG. 28 is a longitudinal side sectional view showing the forward end of a cleaning tube according to a seventh embodiment of the invention.

FIG. 28 shows a seventh embodiment of the invention. According to this embodiment, a cleaning tube of inverse injection type is disclosed as an endoscopic treatment tool.

As shown, the cleaning tube includes a sheath 170 having a flexible tube, a coupling member 178 fixedly forced into the forward end of the sheath 170, a forward-end member 174 mounted rotatably on the coupling member 178 through a connecting member 177, and an operating wire 179 having a torque transmissivity rotatably inserted in the sheath 170.

The forward-end member 174, which is formed in bell shape, includes a small-diameter first inner hole 171 in which the forward end of the operating wire 179 is adapted to be inserted, and a large-diameter second inner hole 172 having a slit 173 in the side wall thereof. The operating wire 179 inserted in the sheath 170 is fixed by brazing or the like method with the forward end thereof inserted in the first inner hole 171 of the forward-end member 174.

The connecting member 177, which is formed in cylindrical shape, includes a forward-end side hole 175 and a base-end side inner hole 176 communicating with each other by fluid. In this case, the longitudinal axis of the forward-end side inner hole 175 is deflected from the longitudinal axis of the connecting member 177. Also, the connecting member 177 has a diagonal facing 185 on the side thereof opposite to the side where the axis of the forward-end side inner hole 175 is deflected.

The forward end of the connecting member 177 is set with an outer diameter permitting insertion into the second inner hole 172 of the forward-end member 174, and is fixed by brazing or the like method as inserted in the second inner hole 172. In fixing the forward-end side of the connecting member 177, the facing 178 and the slit 173 are placed in opposed relation to each other.

Also, the base end of the connecting member 177 has arranged thereon a flange 177a adapted to rotatably engage the engaging section 181 formed at the forward end of the coupling member 178. In this case, the engaging section 181 is formed as a pawl projecting inwardly of the inner hole 180 thereof.

Also, though not shown, the base end side of the sheath 170 has arranged thereon a water socket communicating with the inner hole 180 of the sheath 170. A cleaning liquid is supplied into the inner hole 180 of the sheath 170 through the water supply socket. The cleaning liquid thus supplied is injected diagonally backward from the slit 173 by being guided by the facing 178. Also, the operating wire 179 is adapted to be rotatively operated by the same operating mechanism as any one of the first to fourth embodiments.

The cleaning tube configured as described above is inserted into the channel of the endoscope not shown, and led to the part to be treated in the body cavity through the channel. After that, the operating wire 179 is rotated thereby to rotate the forward end member 174, so that the slit 173 can be oriented in an arbitrary direction. Consequently, the liquid can be supplied in an arbitrary direction through the slit 173 and therefore the desired part in the body cavity can be cleaned.

Figure 29:
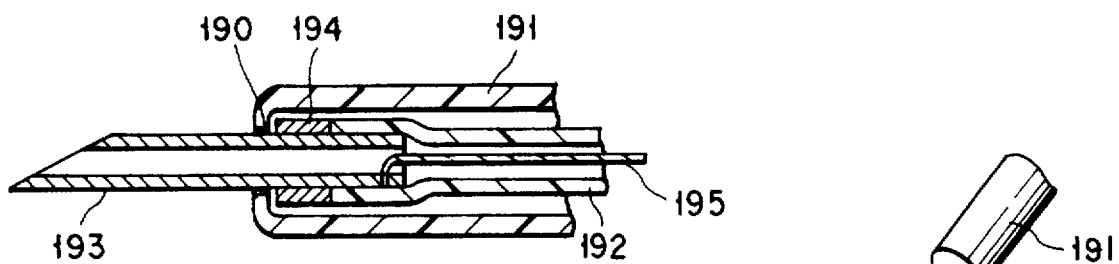
FIG. 29 is a longitudinal side sectional view showing the forward end of an injection needle device according to an eighth embodiment of the invention.
Figure 30A:
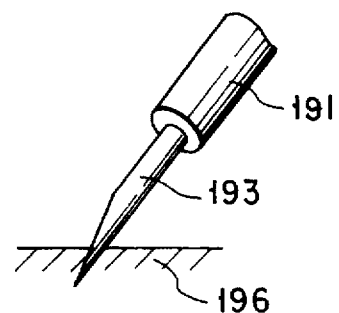
FIGS. 30A and 30B are diagrams for explaining the injection needle device of FIG. 29.
Figure 30B:
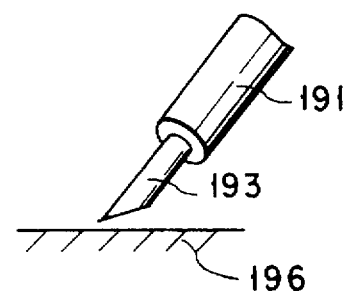

FIGS. 29 and 30A, 30B show an eighth embodiment of the invention. According to the embodiment under consideration, an injection needle device is shown as an endoscopic treatment tool.

As shown, the injection needle device includes an outer sheath 191 made of a flexible tube, and an inner sheath 192 made of a flexible tube inserted retractively into the outer sheath 191. An injection needle 193 with a sharp forward end is forcibly inserted and fixed in the forward end of the inner sheath 192. Also, an operating wire 195 having a torque transmissivity connected to the base end of the needle 193 is inserted into the inner sheath 192.

The forward end of the outer sheath 191 has the inner diameter thereof reduced by thermoforming, thereby forming a thin hole 190 for holding the needle 193 slidably.

Also, a pipe 194 made of stainless steel or the like engaging the thin hole 190 is fixed by soldering or the like on the outer periphery of the needle 193. The overall length of the needle 193 is set in such a manner that the forward end of the pipe 194 is projected by 4 to 8 mm from the forward end of the outer sheath 191 while being engaged in contact with the thin hole 190.

Though not shown, the operating wire 195 is operated retractively and rotatably by the same operating mechanism as any one of the first to fourth embodiments.

The injection needle device having this configuration is inserted into the clamp channel of the endoscope not shown, and is led to the part to be treated in the body cavity through the clamp channel. After that, the operating wire 195 is rotated by the operating mechanism thereby to rotate the inner sheath 192 and the needle 193 with respect to the outer sheath 191, thereby orienting the forward end of the needle 193 in the desired direction.

Specifically, when the needle 193 is pierced into a tissue 196, as shown in FIG. 30A, the forward end of the needle 193 is directed downward. This is because if the needle 193 with the forward end thereof oriented upward is pierced into the tissue 196, the needle 193 would easily slip with the tissue 196, as shown in FIG. 30B. As far as the forward end of the needle 193 can be oriented in an arbitrary direction as according to the present embodiment, therefore, the needle 193 can be accurately pierced into the tissue 193.

Figure 31:
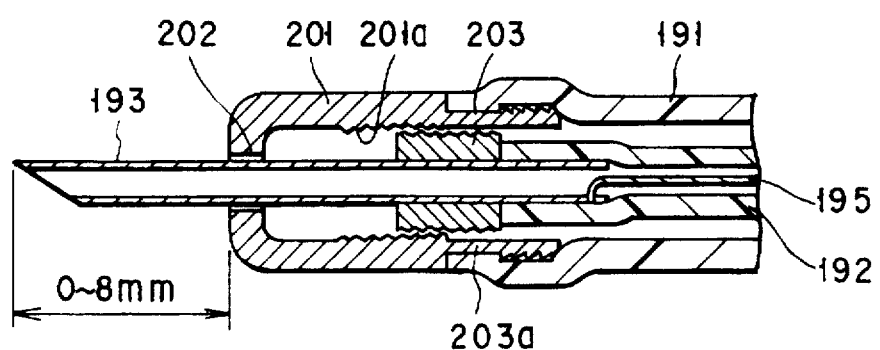
FIG. 31 is a longitudinal side sectional view showing the forward end of an injection needle device according to a ninth embodiment of the invention.

FIG. 31 shows a ninth embodiment of the present invention. This embodiment represents a modification of the eighth embodiment. A injection needle device according to this embodiment includes a cylindrical forward-end member 201 at the forward end of the outer sheath 191. A female screw 201a is formed on the inner surface of the forward-end member 201. This female screw 201a is screwed to a male screw 203a of the engaging member 203 mounted on the outer periphery of the needle 193. By the way, the needle 193 is adapted to project from the forward end of the forward-end member 201 through the thin hole 202 of the forward-end member 201. The configuration of the other component parts of this embodiment is identical to that of the eighth embodiment.

In this configuration, therefore, by changing the amount by which the forward-end member 201 is forced in the engaging member 203 by rotating the operating wire 195, the amount of projection of the needle 202 from the forward-end member 201 can be changed. Preferably, the size of each part is set in such a manner that the amount of projection of the needle 202 from the forward-end member 201 is varied in the range between 0 and 8 mm.

As described above, according to the present embodiment, the following effect is obtained in addition to the effect of the eighth embodiment. More specifically, an injection needle having the desired projection length was conventionally selected and used before the injection needle device is led into the body cavity. According to the present embodiment, by contrast, the projection length of the needle 193 can be adjusted as desired while checking the endoscopic image after leading the injection needle device into the body cavity, and therefore more accurate piercing is made possible. Of course according to the present embodiment, an injection needle having the desired projection length can be selected and used before leading the injection needle device into the body cavity.

Figure 32:
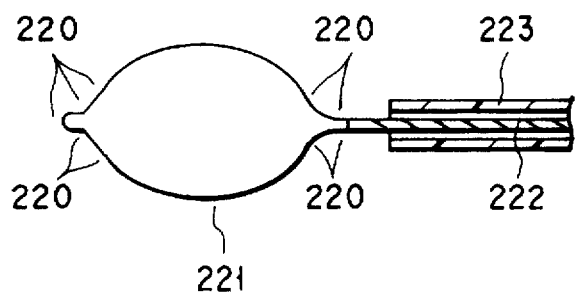
FIG. 32 is a longitudinal side sectional view showing the forward end of a high-frequency incision tool according to a tenth embodiment of the invention.

FIG. 32 shows a tenth embodiment of the invention. According to this embodiment, a high-frequency incision tool is shown as an endoscopic treatment tool.

As shown, the high-frequency incision tool includes a loop section 221 formed in loop by a stainless-steel wire, an operating wire 222 having a torque transmissivity connected to the loop section 221, and an insulatable flexible tube 223 in which the operating wire 222 is inserted.

The loop section 221 can be projected or retracted from the forward end of the tube 223 by push-pull operation of the operating wire 222, thereby opening and closing the particular loop. Also, the loop section 221 has bent portions 220 at a plurality of points, and when being projected from the forward end of the tube 223, is adapted to open widely due to the widening tendency (elasticity) attached to the loop section 221 by the formation of a bent portion 220.

By the way, though not shown, the operating wire 222 is adapted to be retracted and rotatively operated by the same operating mechanism as any one of the first to fourth embodiments.

A high-frequency incision tool having the configuration mentioned above is led into the body cavity by way of endoscope, and then the loop section 221 is projected to open widely from the forward end of the tube 223. Next, the operating wire 222 is rotated and the opening direction of the loop section 221 is adjusted in such a manner that the loop section 221 can be easily caught in a part to be incised such as a polypus. After that, with the loop section 221 caught in the affected part, the operating wire 222 is pulled toward the operator. The affected part thus can be bound by the loop section 221 which is being closed. Under this condition, a high-frequency current is supplied to the loop section 221 from an operating unit not shown through the operating wire 222. The affected part thus is incised as desired.

As described above, according to the present embodiment, the loop surface of the loop section 221 can be oriented in the desire direction, and therefore an affected part such as a polypus can be easily incised.

Figure 33:
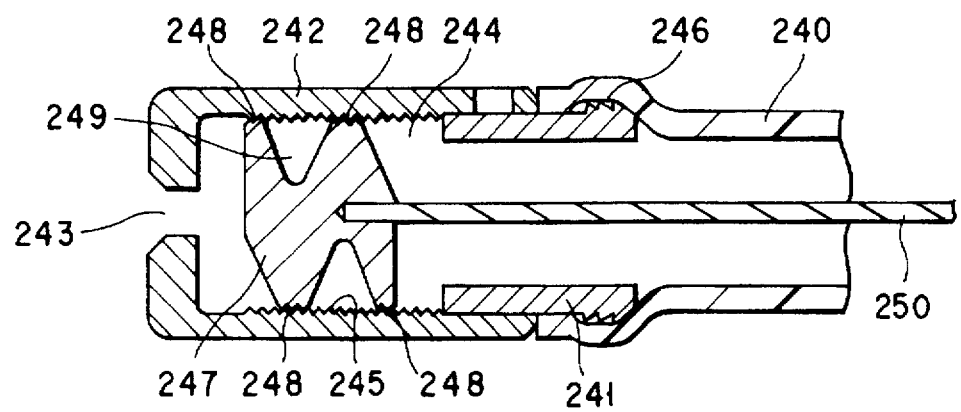
FIG. 33 is a longitudinal side sectional view showing the forward end of a spray-type cleaning tube according to an eleventh embodiment of the invention.

FIG. 33 shows an eleventh embodiment of the present invention. According to this embodiment, a spray-type cleaning tube is disclosed as an endoscopic treatment tool.

As shown, the cleaning tube includes a sheath 240 made of a flexible tube and a cylindrical forward-end member 242 mounted on the forward end of the sheath 240 through a coupling member 241. The coupling member 241 is connected to the forward end of the sheath 240 through an engaging section 246 with a sawtoothed section formed on the outer periphery of the base end.

The forward end member 242 includes a small-diameter hole 243 and a large-diameter hole 244 which has a top 247 built therein. The top 247 is shaped in a round rod, and has on the outer peripheral surface thereof a male screw 248 adapted to be screwed to a female screw 245 formed in the inner surface of the large-diameter hole 244.

Also, a spiral groove 249 deeper than the female screw 248 is formed over the entire length of the outer peripheral surface of the top 247. In this case, the inner hole of the sheath 240 communicates by liquid with the small-diameter hole 243 of the forward-end member 242 by means of the spiral groove 249.

Further, the top 247 has at the base end thereof an operating wire 250 having a torque transmissivity fixedly and rotatably inserted in the sheath 240. Also, a liquid supply cock not shown communicating with the inner hole of the sheath 240 is arranged at the base end of the sheath 240.

By the way, though not shown, the operating wire 250 is adapted to be rotatively operated by means of the same operating mechanism as any one of the first to fourth embodiments.

The cleaning tube having a configuration described above is first led into the body cavity by way of endoscope. The forward end of the cleaning tube (the opening of the small-diameter hole 243) is directed toward the portion to be cleaned and the cleaning liquid is supplied into the sheath 240 from a liquid supply cock. The cleaning liquid thus supplied is caused to flow in eddy when passing through a spiral groove 249 and is expanded into a shower-like form when passing through the small-diameter hole 243 of the forward-end member 242 smaller in diameter than the spiral groove 249. In the process, the top 247 is forced into the forward-end member 242 by rotating the operating wire 250, so that the distance between the forward end of the top 247 and the small-diameter hole 243 undergoes a change. Thus, the angle at which the cleaning liquid spreads out from the small-diameter hole 243 in a shower-like form undergoes a change.

As described above, with the cleaning tube according to the present embodiment, the expansion angle of the cleaning liquid can be changed in accordance with the prevailing situation at the time of spraying the cleaning liquid, and therefore an efficient cleaning operation is made possible.

Figure 34:
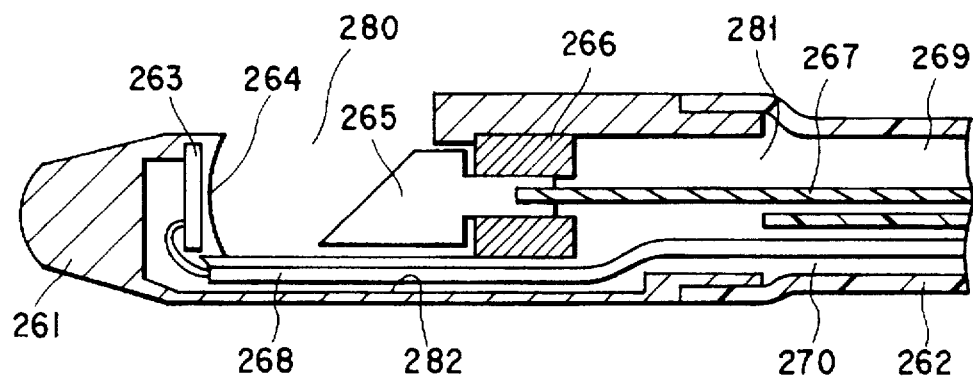
FIG. 34 is a longitudinal side sectional view showing a high-frequency tissue-burning device according to a twelfth embodiment of the invention.
Figure 34:
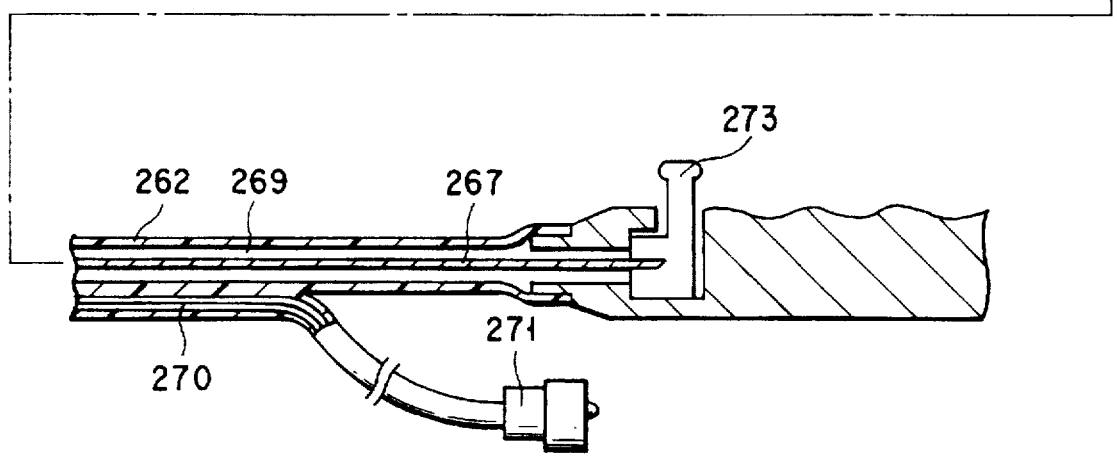

FIG. 34 shows a twelfth embodiment of the invention. According to this embodiment, an ultrasonic tissue-burning device is disclosed as an endoscopic treatment tool.

As shown, an ultrasonic tissue-burning device includes a long lead tube 262 of a flexible material such as resin and a cylindrical forward-end tip 261 mounted at the forward end of the lead tube 262.

The forward-end tip 261 has an inner space 282, which communicates with an external environment through a first opening 280 formed in the side wall of the forward-end tip 261 on one hand and with the inner hole of the lead tube 262 through a second opening 281 formed at the base end thereof.

The forward end of the inner space 282 placed in the vicinity of the first opening 280 has a tabular ultrasonic transducer 263 for transmitting an ultrasonic wave. The ultrasonic transducer 263 is connected with a coaxial cable 268 through a surface electrode not shown.

Also, a concave acoustic lens 264 for converging the ultrasonic wave generated from the ultrasonic transducer 263 is arranged on the front of the ultrasonic transducer 263. In the case where the ultrasonic transducer 263 is in the same shape as a concave lens, the acoustic lens 264 is not required.

Further, a reflective mirror 265 for reflecting the ultrasonic wave generated from the ultrasonic transducer 263 toward the first opening 280 is rotatably arranged at a position opposed to the ultrasonic transducer 263. This reflective mirror 265 is mounted rotatably on the forward-end tip 261 through a slide bearing 266. An operating wire 267 having a torque transmissivity is fixed at the base end of the mirror 265.

The lead tube 262 includes a wire-insertion lumen 269 into which the operating wire 267 is to be inserted and a cable-insertion lumen 270 into which a coaxial cable 268 is to be inserted. The wire-insertion lumen 269 and the cable-insertion lumen 270 branch out as separated members at the base end of the lead tube 262.

A connector 271 is mounted at the base end of the cable-insertion lumen 270 thus branched out. This connector 271 is adapted to be electrically connected to a control unit not shown for controlling the generation of an ultrasonic drive signal. Also, a grip 272 is fixed at the base end of the wire-insertion lumen 269. An operating lever 273 is rotatably arranged on the grip 272. This operating lever 273 has fixed thereon the base end of the operating wire 267.

The ultrasonic tissue-burning device configured as mentioned above is inserted into the body cavity by way of endoscope and has the forward-end tip 261 thereof brought into proximity to the part to be treated. Next, a mirror 265 is observed by a separate endoscope thereby to confirm the relative positions of the part to be treated and the mirror 265, after which the operating lever 273 is rotated to orient the mirror 265 in a predetermined direction. Under this condition, water is supplied to the part to be treated through the endoscope channel, so that the forward-end tip 261 and the part to be treated are immersed in water. Further, under this condition, the ultrasonic transducer 263 is driven and the ultrasonic wave from the ultrasonic transducer 263 is caused to reach the part to be treated by the mirror 265. Consequently, the part to be treated is accurately burned.

As described above, according to this embodiment, the operating lever 273 is manipulated to rotate the mirror 265 in the desired direction. The ultrasonic wave generated from the ultrasonic transducer 263 can thus be rendered to reach the part to be treated accurately. The part to be treated, therefore, can be accurately treated without burning the normal parts other than the part to be treated.

Also, since the ultrasonic transducer 263 is not directly rotated, external forces such as torsion exerted on the coaxial cable 268 is reduced, thereby preventing the cable 268 from breaking.

We claim:

1. An endoscopic treatment tool adapted to be led into a vital body through an endoscope channel and to operate a treatment section by transmitting an operating force of an operating section at an operator's side to the treatment section, the endoscopic treatment tool comprising:

a tubular sheath adapted to be inserted into the endoscope channel;

a rotative operation device arranged on said operating section to rotatively operate said treatment section;

an operating wire rotatably inserted into said tubular sheath for coupling said treatment section with said rotative operation device and having a torque transmissivity capable of transmitting a rotation torque from the rotative operation device to said treatment section;

a lead tube adapted to be inserted into the endoscope channel, said tubular sheath being retractable inserted into said lead tube;

a first slider connected to a base end of said tubular sheath for performing a back-and-forth operation of said tubular sheath with respect to said lead tube; and a second slider connected to a base end of said operating wire and engaging said first slider through a ratchet mechanism for performing a back-and-forth operation of said operating wire while moving back and forth with respect to said first slider.

2. An endoscopic treatment tool according to claim 1, wherein said ratchet mechanism comprises:

an engaging pawl formed along a longitudinal direction of said first slider;

an engaging device arranged in said second slider and adapted to engage said engaging pawl;

a spring for biasing said engaging device with respect to said engaging pawl; and a release button for releasing an engagement between said engaging device and said engaging pawl against the biasing force of said spring.

3. An endoscopic treatment tool according to claim 2, wherein said release button is arranged slidably in said second slider, and a clearance between said release button and said second slider in a direction of advance and retraction of said second slider is 0.01 to 0.2 mm.

4. An endoscopic treatment tool according to claim 2, further comprising a tension release device for releasing a tension of said operating wire by advancing and retracting said second slider with respect to said first slider while holding said first slider and said second slider engaged by said ratchet mechanism.

5. An endoscopic treatment tool according to claim 4, wherein said engaging device maintains a predetermined clearance away from walls of said second slider.

6. An endoscopic treatment tool according to claim 5, wherein said predetermined clearance is 4 to 6 mm.

7. An endoscopic treatment tool according to claim 1, further comprising:

a reinforcing pipe externally arranged at the base end of said operating wire;

a cylindrical support member externally arranged on an outer periphery of said reinforcing pipe, a side of said cylindrical support member being caulked at least at two points in a longitudinal direction of said cylindrical support member, whereby said operating wire, said reinforcing pipe and said support member are integrally fixed, said cylindrical support member is caught in an engaging section arranged in said second slider, and said operating wire and said second slider are rotatably coupled to each other.

8. An endoscopic treatment tool according to claim 7, wherein adjacent caulking operations are performed on opposite sides of said cylindrical support member.

9. An endoscopic treatment tool according to claim 7, further comprising a caulking member comprising a first arm having a recess and a second arm having a protrusion fitted in the recess, and wherein said cylindrical support member is held by said caulking member.

10. An endoscopic treatment tool according to claim 7, wherein adjacent said caulking points are spaced from each other by 0.4 to 0.6 mm in the longitudinal direction of said cylindrical support member.

11. An endoscopic treatment tool according to claim 1, wherein said treatment section includes a holding clamp rotatable with respect to said tubular sheath and adapted to hold a vital tissue, said holding clamp having a holder thereof opening and closing with advance and retraction of said operating wire.

12. An endoscopic treatment tool according to claim 1, wherein said treatment section includes a clip rotatable with respect to said tubular sheath and adapted to widely open due to an inherent widely-opening tendency thereof, said clip being adapted to replaceably engage a hook mounted at a forward end of said operating wire and to close by being retracted into a holding tube mounted replaceably at a forward end of said sheath by a retracting operation of said operating wire.

13. An endoscopic treatment tool according to claim 1, wherein said treatment section includes an incision knife capable of incising tissue by a high-frequency current, said incision knife being rotatable and capable of advancing and retracting with respect to said sheath, said incision knife having a forward end bent at a predetermined angle with respect to a longitudinal axis of said sheath.

14. An endoscopic treatment tool according to claim 13, further comprising an arrangement for restricting an amount by which said incision knife is projected from a forward-end opening of said sheath.

15. An endoscopic treatment tool according to claim 1, wherein said treatment section includes a cleaning liquid injection section rotatable with respect to said sheath and adapted to receive and discharge cleaning liquid supplied thereto through said sheath, said cleaning liquid injection section having a surface for discharging diagonally backward the cleaning liquid supplied thereto through said sheath.

16. An endoscopic treatment tool according to claim 1, wherein said treatment section includes an injection needle for injecting a chemical liquid supplied thereto through said sheath into a vital tissue, said injection needle being rotatable and adapted to advance and retract with respect to said sheath.

17. An endoscopic treatment tool according to claim 16, wherein said injection needle is retractably and rotatably screwed to a forward end of said sheath.

18. An endoscopic treatment tool according to claim 16, further comprising an arrangement for restricting an amount by which the injection needle is projected from a forward-end opening of said sheath.

19. An endoscopic treatment tool according to claim 1, wherein said treatment section comprises a high-frequency snare including a wire closed in a loop section capable of widely opening, said loop section being rotatable and retractable with respect to said sheath, said loop section being pulled into said sheath by a pulling operation of said operating wire so that said loop section is compressed to bind tissue located in said loop section, said bound tissue being burnt off by high-frequency current supplied through said operating wire.

20. An endoscopic treatment tool according to claim 1, wherein said treatment section comprises a high-frequency marking section including a marking ring member and a base end, said marking section formed from a shape memory alloy for storing an annular shape of said ring member and an angle $\alpha$ of an axis extending from a root of said ring member to a remainder of said ring member, said marking section being rotatable and retractable with respect to said sheath and capable of being pulled into said sheath by deforming the ring member in linear fashion, said marking section being adapted to provide an annular marking on tissue against which the ring member is pressed by supplying a high-frequency current to said marking section through said operating wire.

21. An endoscopic treatment tool according to claim 1, wherein:

a cleaning liquid injection member is arranged at a forward end of said sheath for receiving and discharging a cleaning liquid supplied through said sheath, which cleaning liquid injection member has an opening for forward discharging the cleaning liquid supplied thereto through said sheath, and said treatment section includes a top adapted to advance and retract with respect to said opening, said top including a guide groove for spirally supplying the cleaning liquid supplied thereto through said sheath toward said opening, said top being screwed retractively to said cleaning liquid injection member.

22. An endoscopic treatment tool according to claim 1, wherein a forward end of said sheath has fixed thereon a cylindrical forward-end tip having an internal space communicating with an external environment at a first opening formed in a side wall of said forward-end tip, said internal space also communicating with an inner hole of said sheath at a second opening formed at a base end thereof, further comprising an ultrasonic transducer arranged on a forward end side of said internal space located in proximity to said first opening for transmitting an ultrasonic wave, and wherein said treatment section is a reflective mirror rotatably mounted on said sheath in opposed relation to said ultrasonic transducer, said reflective mirror being adapted to reflect an ultrasonic wave generated from said ultrasonic transducer toward said first opening.

23. An endoscopic treatment tool according to claim 17, further comprising an arrangement for restricting an amount by which the injection needle is projected from a forward-end opening of said sheath.

* * * * *